(12) United States Patent
Reid et al.

(10) Patent No.: US 12,150,967 B2
(45) Date of Patent: Nov. 26, 2024

(54) METHODS AND COMPOSITIONS FOR HONEY BEE HEALTH

(71) Applicant: SEED HEALTH, INC., Venice, CA (US)

(72) Inventors: Gregor Reid, Arva (CA); Brendan Daisley, London (CA); Raja Dhir, Venice, CA (US)

(73) Assignee: Seed Health, Inc., Venice (CA)

( * ) Notice: Subject to any disclaimer, the term of this patent is extended or adjusted under 35 U.S.C. 154(b) by 613 days.

(21) Appl. No.: 17/269,135

(22) PCT Filed: Aug. 19, 2019

(86) PCT No.: PCT/US2019/047059
§ 371 (c)(1),
(2) Date: Feb. 17, 2021

(87) PCT Pub. No.: WO2020/055547
PCT Pub. Date: Mar. 19, 2020

(65) Prior Publication Data
US 2022/0211777 A1    Jul. 7, 2022

Related U.S. Application Data

(60) Provisional application No. 62/765,004, filed on Aug. 18, 2018.

(51) Int. Cl.
| A61K 35/747 | (2015.01) |
| A23K 10/18 | (2016.01) |
| A23K 10/38 | (2016.01) |
| A23K 20/163 | (2016.01) |
| A23K 50/90 | (2016.01) |
| A61K 9/00 | (2006.01) |
| A61K 35/00 | (2006.01) |
| A61P 31/00 | (2006.01) |

(52) U.S. Cl.
CPC ............ *A61K 35/747* (2013.01); *A23K 10/18* (2016.05); *A23K 10/38* (2016.05); *A23K 20/163* (2016.05); *A23K 50/90* (2016.05); *A61K 9/0056* (2013.01); *A61P 31/00* (2018.01); *A23V 2400/169* (2023.08); *A23V 2400/175* (2023.08); *A61K 2035/115* (2013.01)

(58) Field of Classification Search
None
See application file for complete search history.

(56) References Cited

U.S. PATENT DOCUMENTS

| 3,178,341 | A | 4/1965 | Hamill et al. |
|---|---|---|---|
| 3,832,460 | A | 8/1974 | Kosti |
| 4,136,162 | A | 1/1979 | Fuchs et al. |
| 4,163,777 | A | 8/1979 | Mitra |
| 4,687,841 | A | 8/1987 | Spilburg et al. |
| 4,720,486 | A | 1/1988 | Spilburg et al. |
| 5,002,970 | A | 3/1991 | Eby, III |
| 5,158,789 | A | 10/1992 | DuRoss |
| 5,719,196 | A | 2/1998 | Uhari et al. |
| 5,895,648 | A | 4/1999 | Cavaliere Vesely et al. |
| 6,054,143 | A | 4/2000 | Jones |
| 6,139,861 | A | 10/2000 | Friedman |
| 6,210,699 | B1 | 4/2001 | Acharya et al. |
| 6,287,610 | B1 | 9/2001 | Bowling et al. |
| 6,569,474 | B2 | 5/2003 | Clayton et al. |
| 6,599,883 | B1 | 7/2003 | Romeo et al. |
| 6,919,373 | B1 | 7/2005 | Lam et al. |
| 7,087,249 | B2 | 8/2006 | Burrell et al. |
| 7,267,975 | B2 | 9/2007 | Strobel et al. |
| 7,820,420 | B2 | 10/2010 | Whitlock |
| 7,846,711 | B2 | 12/2010 | Boettner et al. |
| 8,349,313 | B2 | 1/2013 | Smith et al. |
| 8,383,201 | B2 | 2/2013 | Berry et al. |
| 8,481,299 | B2 | 7/2013 | Gueniche |
| 8,496,914 | B2 | 7/2013 | Bonfiglio |
| 8,585,588 | B2 | 11/2013 | Kovarik et al. |
| 8,685,389 | B2 | 4/2014 | Baur |
| 8,701,671 | B2 | 4/2014 | Kovarik |
| 8,716,327 | B2 | 5/2014 | Zhao et al. |
| 8,758,764 | B2 | 6/2014 | Masignani et al. |
| 8,815,538 | B2 | 8/2014 | Lanzalaco et al. |

(Continued)

FOREIGN PATENT DOCUMENTS

| CN | 103937722 | 7/2014 |
|---|---|---|
| WO | WO 2009/052421 | 4/2009 |

(Continued)

OTHER PUBLICATIONS

Borges, "Control of the intestinal parasite *Nosema ceranae* in *Apis mellifera* using nutraceuticals, prebiotics and probiotics", M.S. Thesis, University of Guelph, Ontario, Canada. (Year: 2015).*
Degrandi-Hoffman et al., Journal of Apircultural Research and Bee World, vol. 47(4), pp. 265-270. (Year: 2008).*
Irandoust et al. (International Journal of Advanced Biological and Biomedical Research, vol. 1, Issue 6, pp. 601-613. (Year: 2013).*
Shimanuki et al., "Diagnosis of Honey Bee Diseases", USDA Agricultural Handbook, No. 690, pp. 1-63. (Year: 2000).*

(Continued)

*Primary Examiner* — Michelle F. Paguio Frising
*Assistant Examiner* — Grant C Currens
(74) *Attorney, Agent, or Firm* — Sheridan Ross P.C.

(57) ABSTRACT

The present disclosure relates to compositions, methods and systems for the prophylaxis and treatment of honey bees (e.g. *Apis mellifera*) to protect and/or treat certain diseases, disorders and conditions, e.g., Colony Collapse Disorder and American foulbrood. The present disclosure comprises probiotic compositions, and methods of use thereof, for administration to honey bees for the purposes of treating or preventing disease.

10 Claims, 22 Drawing Sheets
Specification includes a Sequence Listing.

(56) References Cited

U.S. PATENT DOCUMENTS

| | | |
|---|---|---|
| 8,865,211 B2 | 10/2014 | Tzannis et al. |
| 8,951,775 B2 | 2/2015 | Castiel |
| 8,999,372 B2 | 4/2015 | Davidson et al. |
| 9,011,834 B1 | 4/2015 | McKenzie et al. |
| 9,017,718 B2 | 4/2015 | Tan et al. |
| 9,028,841 B2 | 5/2015 | Henn et al. |
| 9,131,884 B2 | 9/2015 | Holmes |
| 9,234,204 B2 | 1/2016 | Qvit-Raz et al. |
| 9,288,981 B2 | 3/2016 | Gandhi et al. |
| 10,586,916 B2 | 2/2020 | Kovarik |
| 10,675,347 B2 | 6/2020 | Kovarik |
| 10,933,128 B2 | 3/2021 | Kovarik |
| 11,529,412 B2 | 12/2022 | Kovarik |
| 2002/0009436 A1 | 1/2002 | Doyle et al. |
| 2002/0022057 A1 | 2/2002 | Battey et al. |
| 2003/0031737 A1 | 2/2003 | Rosenbloom |
| 2003/0124178 A1 | 7/2003 | Haley |
| 2003/0206995 A1 | 11/2003 | Bowling et al. |
| 2004/0096569 A1 | 5/2004 | Barkalow et al. |
| 2004/0120991 A1 | 6/2004 | Gardner et al. |
| 2004/0136923 A1 | 7/2004 | Davidson |
| 2004/0228804 A1 | 11/2004 | Jones et al. |
| 2005/0100559 A1 | 5/2005 | Myatt et al. |
| 2005/0196358 A1 | 9/2005 | Georgiades et al. |
| 2006/0035008 A1 | 2/2006 | Virgallito et al. |
| 2006/0204591 A1 | 9/2006 | Burrell et al. |
| 2007/0054008 A1 | 3/2007 | Clayton et al. |
| 2007/0207955 A1 | 9/2007 | Tanihara et al. |
| 2007/0218114 A1 | 9/2007 | Duggan et al. |
| 2007/0293587 A1 | 12/2007 | Haley |
| 2008/0267933 A1 | 10/2008 | Ohlson et al. |
| 2009/0196907 A1 | 8/2009 | Bunick et al. |
| 2009/0196908 A1 | 8/2009 | Lee et al. |
| 2009/0205083 A1 | 8/2009 | Gupta et al. |
| 2010/0029832 A1 | 2/2010 | Pinnavaia et al. |
| 2010/0285098 A1 | 11/2010 | Haley |
| 2011/0142942 A1 | 6/2011 | Schobel et al. |
| 2011/0217368 A1 | 9/2011 | Prakash et al. |
| 2011/0269119 A1 | 11/2011 | Hutchison et al. |
| 2012/0027786 A1 | 2/2012 | Gupta |
| 2012/0058094 A1 | 3/2012 | Blaser et al. |
| 2012/0142548 A1 | 6/2012 | Corsi et al. |
| 2012/0276143 A1 | 11/2012 | O'Mahony et al. |
| 2012/0276525 A1 | 11/2012 | Kovarik et al. |
| 2013/0064796 A1 | 3/2013 | Hamdi et al. |
| 2013/0157876 A1 | 6/2013 | Lynch et al. |
| 2013/0259834 A1 | 10/2013 | Klaenhammer et al. |
| 2013/0315869 A1 | 11/2013 | Qimron et al. |
| 2014/0044677 A1 | 2/2014 | Qvit-Raz et al. |
| 2014/0044734 A1 | 2/2014 | Sverdlov et al. |
| 2014/0045744 A1 | 2/2014 | Gordon |
| 2014/0065209 A1 | 3/2014 | Putaala et al. |
| 2014/0065218 A1 | 3/2014 | Lang et al. |
| 2014/0068797 A1 | 3/2014 | Doudna et al. |
| 2014/0154290 A1 | 6/2014 | Peters et al. |
| 2014/0199266 A1 | 7/2014 | Park et al. |
| 2014/0199281 A1 | 7/2014 | Henn et al. |
| 2014/0212520 A1 | 7/2014 | Del Vecchio |
| 2014/0255351 A1 | 9/2014 | Berstad et al. |
| 2014/0271867 A1 | 9/2014 | Myers |
| 2014/0333003 A1 | 11/2014 | Allen et al. |
| 2014/0349405 A1 | 11/2014 | Sontheimer et al. |
| 2014/0356460 A1 | 12/2014 | Lutin |
| 2014/0363441 A1 | 12/2014 | Grandea, III et al. |
| 2014/0377278 A1 | 12/2014 | Elinav et al. |
| 2015/0017227 A1 | 1/2015 | Kim |
| 2015/0038594 A1 | 2/2015 | Borges et al. |
| 2015/0064138 A1 | 3/2015 | Lu et al. |
| 2015/0071957 A1 | 3/2015 | Kelly |
| 2015/0086581 A1 | 3/2015 | Li et al. |
| 2015/0093473 A1 | 4/2015 | Barrangou |
| 2015/0132263 A1 | 5/2015 | Liu et al. |
| 2015/0150792 A1 | 6/2015 | Klingman |
| 2015/0166641 A1 | 6/2015 | Goodman |
| 2015/0190435 A1 | 7/2015 | Henn et al. |
| 2015/0216917 A1 | 8/2015 | Jones |
| 2015/0329555 A1 | 11/2015 | Liras et al. |
| 2015/0329875 A1 | 11/2015 | Gregory et al. |
| 2015/0352023 A1 | 12/2015 | Berg et al. |
| 2015/0353901 A1 | 12/2015 | Liu |
| 2015/0361436 A1 | 12/2015 | Hitchcock |
| 2015/0374607 A1 | 12/2015 | Lanzalaco et al. |
| 2016/0008412 A1 | 1/2016 | Putaala et al. |
| 2016/0024510 A1 | 1/2016 | Bikard et al. |
| 2016/0040216 A1 | 2/2016 | Wilder |
| 2016/0089315 A1 | 3/2016 | Kleinberg et al. |
| 2016/0151427 A1 | 6/2016 | Whitlock et al. |
| 2016/0168594 A1 | 6/2016 | Zhang et al. |
| 2016/0206668 A1 | 7/2016 | Kort et al. |
| 2016/0271106 A1 | 9/2016 | Shi et al. |
| 2016/0271189 A1 | 9/2016 | Cutcliffe |
| 2016/0314281 A1 | 10/2016 | Apte |
| 2016/0348120 A1 | 12/2016 | Esvelt et al. |
| 2016/0354416 A1 | 12/2016 | Gajewski et al. |
| 2017/0020932 A1 | 1/2017 | Cutcliffe et al. |
| 2017/0021011 A1 | 1/2017 | Kovarik et al. |
| 2017/0035820 A1 | 2/2017 | Stamets et al. |
| 2017/0071986 A1 | 3/2017 | Kovarik et al. |
| 2017/0151293 A1 | 6/2017 | Kovarik |
| 2018/0020678 A1 | 1/2018 | Scharf et al. |
| 2018/0119132 A1 | 5/2018 | Hutchinson et al. |
| 2018/0177160 A1 | 6/2018 | Wagoner et al. |
| 2018/0216123 A1 | 8/2018 | Anand et al. |
| 2019/0015528 A1 | 1/2019 | Moran et al. |
| 2019/0177807 A1 | 6/2019 | Wan et al. |
| 2019/0321417 A1 | 10/2019 | Brucker et al. |
| 2020/0318139 A1 | 10/2020 | Gersbach et al. |
| 2022/0175914 A1 | 6/2022 | Kovarik |

FOREIGN PATENT DOCUMENTS

| | | | |
|---|---|---|---|
| WO | WO 2010/146405 | 12/2010 | |
| WO | WO 2011/138310 | 11/2011 | |
| WO | WO 2013/026000 | 2/2013 | |
| WO | WO 2014/182632 | 11/2014 | |
| WO | WO 2017/040343 | 3/2017 | |
| WO | WO-2018140479 A1 * | 8/2018 | ............. A01G 31/00 |

OTHER PUBLICATIONS

Vanengelsdorp et al., "Colony Collapse Disorder: A Descriptive Study", PLOS One, vol. 4, Issue 8, pp. 1-17. (Year: 2009).*

Song et al.. "Characterization of Selected Lactobacillus Strains for Use as Probiotics", Korean Journal for Food Science of Animal Resources, vol. 35, No. 4, p. 551-556. (Year: 2015).*

Glavinic et al. "Dietary amino acid and vitamin complex protects honey bee from immunosuppression caused by Nosema ceranae", PLOS One, vol. 12, No. 11. p. 1-18 (Year: 2017).*

Arredondo et al., "Lactobacillus kunkeei strains decreased the infection by honey bee pathogens *Paenibacillus larvae* and *Nosema ceranae*," Beneficial Microbes, Feb. 2018, 9(2):279-90.

Daisley et al., "Microbiota-mediated modulation of organophosphate insecticide toxicity by species-dependent interactions with Lactobacilli in a Drosophila melanogaster insect model," Applied & Environmental Microbiology, May 2018, 84(9).

Daisley et al., "Neonicotinoid-induced pathogen susceptibility is mitigated by Lactobacillus plantarum immune stimulation in a Drosophila melanogaster model," Scientific Reports, Jun. 2017, 13 pages.

PCT International Preliminary Report on Patentability in International Appln. No. PCT/US19/47059, dated Mar. 4, 2021, 10 pages.

PCT International Search Report and Written Opinion in International Appln. No. PCT/US19/47059, dated Mar. 24, 2020, 19 pages.

Rangberg et al., "The paratransgenic potential of Lactobacillus kunkeei in the honey bee *Apis mellifera*," Beneficial Microbes, Aug. 2015, 6(4):513-23.

Trinder et al., "Probiotic Lactobacillus rhamnosus reduces organophosphate pesticide absorption and toxicity to Drosophila melanogaster," Applied and environmental microbiology, Oct. 2016, 82(20):6204-13.

(56) References Cited

OTHER PUBLICATIONS

Vásquez et al., "Symbionts as major modulators of insect health: lactic acid bacteria and honeybees," PloS one, Mar. 2012, 7(3):e33188.
Bustin et al., "The MIQE guidelines: Minimum Information for Publication of Quantitative Real-Time PCR Experiments," Clin Chem., 2009, 12 pages.
Callahan et al., "Exact sequence variants should replace operational taxonomic units in marker-gene data analysis," The ISME Journal, Dec. 2017, 11(12):2639-43, 5 pages.
Daisley et al., "Microbiota-mediated modulation of organophosphate insecticide toxicity by species-dependent interactions with *Lactobacilli* in a *Drosophila melanogaster* insect model," Applied and environmental microbiology, May 2018, 13 pages.
De Graaf et al., "Standard methods for American foulbrood research," Journal of Apicultural Research, Jan. 2013, 29 pages.
Gloor et al., "Compositional analysis: a valid approach to analyze microbiome high-throughput sequencing data," Canadian journal of microbiology, Apr. 2016, 12 pages.
Harpur et al., "No genetic tradeoffs between hygienic behavior and individual innate immunity in the honey bee, Apis mellifera," PloS one, Aug. 2014, 9(8):e104214, 7 pages.
Newton et al., "The effect of training set on the classification of honey bee gut microbiota using the Naive Bayesian Classifier," BMC microbiology, Dec. 2012, 9 pages.
Okuyama et al., "The complete mitochondrial genome of a Buckfast bee, *Apis mellifera* (Insecta: Hymenoptera: Apidae) in Northern Ireland," Mitochondrial DNA Part B, Jan. 2018, 3 pages.
Powell et al., "Routes of acquisition of the gut microbiota of the honey bee *Apis mellifera*," Applied and environmental microbiology, Dec. 2014, 10 pages.
Smart et al., "Linking measures of colony and individual honey bee health to survival among apiaries exposed to varying agricultural land use," PloS one, Mar. 2016, 11(3):e0152685, 28 pages.
Standifer et al., "Supplemental feeding of honey bee colonies," Department of Agriculture, Science and Education Administration, Jun. 1978, 12 pages.
Versalovic et al., "Genomic fingerprinting of bacteria using repetitive sequence-based polymerase chain reaction," Methods in molecular and cellular biology, Jan. 1994, 16 pages.
"CRISPR/Cas9 & Targeted Genome Editing: New Era in Molecular Biology," New England Biolabs, publication date unknown, retrieved Aug. 22, 2019 from https://www.neb.com/en-us/tools-and-resources/feature-articles/crispr-cas9-and-targeted-genome-editing-a-new-era-in-molecular-biology, 7 pages.
"Probeeotics UBC Igem 2015," Team British Columbia, 2015, 46 pages.
"Welcome to the UBC Igem Wiki," Team British Columbia, 2015, retrieved Oct. 16, 2017 from http://2015.igem.org/Team:British_Columbia, 4 pages.
Chmiel et al., "Understanding the Effects of Sublethal Pesticide Exposure on Honey Bees: A Role for Probiotics as Mediators of Environmental Stress," Frontiers in Ecology and Education, vol. 8, No. 22, Feb. 2020, 19 pages.

Daisley et al., "Novel probiotic approach to counter Paenibacillus larvae infection in honey bees," The ISME Journal, vol. 14, Oct. 29, 2019, pp. 476-491.
Gong et al., "An engineered Pseudomonas putida can simultaneously degrade organophosphates, pyrethroids and carbamates," Science of The Total Environment, vol. 628-629, Jul. 1, 2018, pp. 1258-1265. Abstract only.
Huang et al., "Genome Sequencing and Comparative Analysis of Stenotrophomonas acidaminiphila Reveal Evolutionary Insights Into Sulfamethoxazole Resistance," Frontiers In Microbiology, vol. 9, No. 1013, May 17, 2018, 25 pages.
Itoh et al., "Detoxifying symbiosis: microbe-mediated detoxification of phytotoxins and pesticides in insects," Natural Product Reports, vol. 35, No. 5, May 25, 2018, pp. 434-454. Abstract only.
Kumar et al., "Biodegradation of Fipronil by *Paracoccus* sp. In Different Types of Soil," Bulletin of Environmental Contamination and Toxicology, vol. 88, No. 5, May 2012, pp. 781-787. Abstract only.
Li et al., "Molecular cloning and characterization of a novel pyrethroid-hydrolyzing esterase originating from the metagenome," Microbial Cell Factories, vol. 7, No. 38, Dec. 30, 2008, 17 pages.
Mandal et al., "Microbial degradation of fipronil by Bacillus thuringiensis," Ecotoxicology and Environmental Safety, vol. 93, Jul. 1, 2013, pp. 87-92. Abstract only.
Medhi et al., "Genome Sequence of a Heterotrophic Nitrifier and Aerobic Dentrifier, Paracoccus denitrificans Strain ISTOD1, Isolated from Wastewater," Genome Announcements, vol. 6, No. 15, Apr. 2018, 4 pages.
Pankaj et al., "Novel pathway of cypermethrin biodegradation in a *Bacillus* sp. Strain SG2 isolated from cypermethrin-contaminated agriculture field," 3 Biotech, vol. 6, No. 45, Feb. 4, 2016, 11 pages.
Smith et al., "Genomic signatures of honey bee association in an acetic acid symbiont," bioRxiv Preprint, Jul. 11, 2018, 31 pages.
Uniyal et al., "Degradation of fipronil by Strenotrophomonas acidaminiphila isolated from rhizospheric soil of *Zea mays*," 3 Biotech, vol. 6, No. 48, Jun. 2016, 26 pages.
Wang et al., "Bacterial Genome Editing with CRISPR-Cas9: Deletion, Integration, Single Nucleotide Modification, and Desirable "Clean" Mutant Selection in Clostridium beijerinckii as an Example," ACS Synthetic Biology, vol. 5, Apr. 2016, pp. 721-732.
Wang et al., "Cloning of a novel pyrethroid-hydrolyzing carboxylesterase gene from *Sphingobium* sp. JZ-1 and characterization of the gene product," Applied and Environmental Microbiology, vol. 75, No. 17, Sep. 2009, pp. 5496-5500.
Wu et al., "Molecular cloning, purification, and biochemical characterization of a novel pyrethroid- hydrolyzing esterase from *Klebsiella* sp. strain ZD112," Journal of Agricultural and Food Chemistry, vol. 54, No. 3, Jan. 4, 2006, pp. 836-842. Abstract only.
Zhai et al., "Molecular cloning, purification and biochemical characterization of a novel pyrethroid-hydrolyzing carboxylesterase gene from Ochrobactrum anthropi YZ-1," Journal of Hazardous Materials, vol. 221-222, Jun. 30, 2012, pp. 206-212.

\* cited by examiner

| Target | NCBI ID | Forward Sequence (5'-3') | Reverse Sequence (5'-3') |
|---|---|---|---|
| B-actin | NM_001185146 | TTGTATGCCAACACTGTCCTTT | TGGCGCGATGATCTTAATTT |
| Rp55 | XM_006570237 | AATTATTGGTGCTGGAATTG | TAACGTCCAGCAGAATGTGGTA |
| Alphaproteobacteria | TXID_28211 | CTAGTGTAGAGGTGAAATTC | CCCCGTCAATTCCTTTGAGTT |
| Betaproteobacteria | TXID_28216 | CTTAGAGATAGGAGAGTG | TAATGATGGCAACTAATGACAA |
| Gammaproteobacteria | TXID_1236 | TCGTCAGCTCGTGTYGTGA | CGTAAGGGCCATGATG |
| Actinobacteria | TXID_201174 | TACGGCCGCAAGGCTA | TCRTCCCACCTTCCTCG |
| Bacteroidetes | TXID_976 | CRAACAGGATTAGATACCCT | GGTAAGGTTCCTCGCGTAT |
| Firmicutes | TXID_1239 | TGAAACTYAAAGGAATTGACG | ACCATGCACCACCTGTC |
| Paenibacillus larvae | TXID_1464 | CGGGAGACGCCAGGTTAG | TTCTTCCTTGGCAACAGAGC |
| Lactobacillus plantarum | TXID_1590 | ATTCATAGTCTAGTTGGAGGT | CCTGAACTGAGAGAATTTGA |
| Lactobacillus rhamnosus | TXID_47715 | TGCTTGCATCTTGATTAATTTG | GGTTCTTGGATYTATGCGGTATTAG |
| Lactobacillus kunkeei | TXID_148814 | GAGAAGCATTACTAAGCCAAC | CATATTGACCTTACCACCAGAT |
| Escherichia coli | TXID_562 | TGATTGGCAAAATCTGGCCG | GAAATCGCCCAAATCGCCAT |

FIG. 11

| Target | NCBI ID | Forward sequence (5'-3') | Reverse sequence (5'-3') |
|---|---|---|---|
| Alpha-tubulin | XM_623217 | GCACGTGAAGATTCTAGCAGTC | GCACCTTCTCCTTCACCTTCAG |
| Rp5S | XM_624081 | AATTATTGGTCGCTGGAATTG | TAACGTCCAGCAGAATGGTA |
| Microsomal glutathione-S-transferase | XM_394313 | TTGCTCTGTAAGGTTGTTTTGC | TGTCTGGTAACTACAAATCTTCTG |
| Glucuronyltransferase | XM_392727 | CACGGATACATCCTGCAGTCATC | GAGAATGACGAGATACAGAACTGTCAC |
| Defensin-1 | NM_001011616 | TGCGCTGCTAACTGTCTCAG | AATGGCACTTAACCGAAACG |
| Defensin-2 | XM_396841 | GCAACTACCGCCTTTACGTC | GGGTAACGTGCGACGTTTA |
| Prophenol oxidase | XM_392817 | AGATGGCATGCATTGTTGTTGA | CCACGTCGTCTTCTTTAGG |
| Hymenoptaecin | NM_001011615 | CTCTCTGTGCCGTTGCATA | CGTCTCCTGTCATTCCATT |
| Pentrophin/chitin binding domain | XM_003250167 | GCAAACGAGAGATTCAATGGCAATCTTCAG | CACATTGGTAATTGTATAGTACGTTCCATC |
| Apisimin | XM_003249457 | TGAGCAAAATGTTGCTGTC | AACGACATCACGTTCGATT |
| MARVL | XM_391948 | GAAATGTTGAATACATCGATATTCACCGTAC | CTCCATTCCAGTAGAGGAAGTATGTC |
| Cyp9q1 | XM_393971 | ATCCTGGCCAAGTGCAGCTTC | CAGCTCCTTCAATTGGATCAGCAAC |

FIG. 12

METHODS AND COMPOSITIONS FOR HONEY BEE HEALTH

CROSS REFERENCE

The present disclosure claims the benefit of U.S. Provisional Application No. 62/765,004, filed Aug. 18, 2018, which is incorporated herein by reference in its entirety.

TECHNICAL FIELD

The present disclosure relates to compositions, methods, and systems for the prophylaxis and treatment of honey bees (e.g., *Apis mellifera*) to protect and/or treat certain diseases, disorders and conditions, e.g., Colony Collapse Disorder and American foulbrood.

SEQUENCE LISTING

This application contains a sequence listing submitted to the United States Patent and Trademark Office via the electronic filing system as an ASCII text file. The sequence listing, which is incorporated-by-reference herein, is titled "Sequence_Listing.txt," was created on Jun. 14, 2021 and amended on Sep. 13, 2021, and has a size of 5,085 bytes.

BACKGROUND

Pollinating insects are key to the evolutionary and ecological success of flowering plants and enable much of the diversity in the human diet. Bees are arguably one of the most important beneficial insects worldwide. Their positive impact can be measured by the value they contribute to the agricultural economy, their ecological role in providing pollination services, and the hive products they produce. The honey bee is credited with approximately 85% of the pollinating activity necessary to supply about one-quarter to one-third of the nation's food supply. Over 50 major crops in the United States either depend on honey bees for pollination or produce more abundantly when honey bees are plentiful.

Bees are vital to global biodiversity and food security through their pollination of plants, including several key crops. Honey bees, however, are exposed to myriad of stressors including pests, pathogens, pesticides, poor nutrition due to monocropping and habitat loss leading to extreme colony losses.

SUMMARY

Disclosed herein are compositions, methods and systems for the prophylaxis and treatment of insects, such as honey bees (e.g. *Apis mellifera*), to protect and/or treat certain diseases, disorders and conditions. Thus, in one aspect, provided herein is a composition for protecting honeybees from pesticides and pathogens, comprising at least one *Lactobacillus* strain. In some embodiments, the at least one *Lactobacillus* strain is selected from the group consisting of: *Lactobacillus rhamnosus* GR-1, *Lactobacillus plantarum* Lp39, and *Lactobacillus kunkeei* BR-1. In some embodiments, the composition comprises *Lactobacillus rhamnosus* GR-1, *Lactobacillus plantarum* Lp39, *Lactobacillus kunkeei* BR-1, or combinations thereof.

In some embodiments disclosed herein is pollen patty composition comprising a carbohydrate or sugar source, a protein source, and an effective amount of *Lactobacillus rhamnosus* GR-1, *Lactobacillus plantarum* Lp39, *Lactobacillus kunkeei* BR-1, or combinations thereof.

In some embodiments, the composition provided herein includes a carbohydrate or sugar source, a protein source, and an effective amount of *Lactobacillus rhamnosus* GR-1, *Lactobacillus plantarum* Lp39, *Lactobacillus kunkeei* BR-1, or combinations thereof. In various embodiments, the composition is a pollen patty. In some embodiments, the sugar source is a sugar syrup, solid sugar, or a combination thereof. In some embodiments, the protein source is soy flour, nutritional yeast, Brewer's yeast, yeast-extract, or combinations thereof. In some embodiments, the pollen patty includes bee pollen. In some embodiments, the composition includes an antioxidant, an oil, a preservative, or combinations thereof.

In another aspect, included herein are methods of manufacturing the pollen patty composition, comprising contacting a pollen patty with an effective amount of *Lactobacillus rhamnosus* GR-1, *Lactobacillus plantarum* Lp39, and *Lactobacillus kunkeei* BR-1.

Also envisioned herein are kits for constructing a pollen patty. In some embodiments, the kit comprises a container of dry sugar and/or protein source, a vial comprising an effective amount of stabilized *Lactobacillus rhamnosus* GR-1, *Lactobacillus plantarum* Lp39, and *Lactobacillus kunkeei* BR-1, and an optional container of liquid and/or syrup.

In another aspect, methods are provided for using the compositions disclosed herein, wherein in some embodiments, the composition is formulated for distribution as a pollen patty.

In some embodiments, the composition is formulated for application as an isotonic liquid solution.

BRIEF DESCRIPTION OF DRAWINGS

FIG. 1A shows the molecular identification of *Paenibacillus larvae* BMR43-81 by rep-PCR using ERIC primers. Red arrow=970 bp confirmation band for *P. larvae* subsp. larvae. Black arrows=Characteristic banding pattern for previously established ERIC subtype I profile. FIG. 1B shows a pathogen load of whole honey bee larvae from inner brood frames of experimental hives was determined by plating extracted homogenates on MY agar media. Colony forming units (CFU) obtained represent the mean±standard deviation (one-way ANOVA with Tukey's multiple comparisons) of n=10 pooled larval samples for each treatment group (3 larvae per pooled sample). FIG. 1C shows the pathogen activity of whole honey bee larvae from inner brood frames of experimental hives was determined via a modified Holst milk test clearance assay. Mean casein hydrolysis±standard deviation (one-way ANOVA with Tukey's multiple comparisons) of n=6 pooled larval samples for each treatment group (3 larvae per pooled sample) with triplicate technical repeats are shown. FIGS. 1D-E show qPCR-based quantification of dominant microbiota phylotypes and supplemental lactobacilli across treatment groups. Data represents the median (line in box), IQR (box) and minimum/maximum (whiskers) of n=6 pooled larval samples for each treatment group (3 larvae per pooled sample) with duplicate technical repeats. Statistical comparisons shown for one-way ANOVA (dominant microbiota phylotypes) and Kruskal-Wallis (supplemental lactobacilli) tests with Dunnett's and Dunn's multiple comparisons, respectively. ns=not significant, *$p<0.05$, $p<0.01$, *$p<0.001$, and ****$p<0.0001$.

FIG. 2C shows Bar plots represent the gut microbiota compositions of a single bee from each of their respective treatment groups as determined by sequencing of the V4 region of the bacterial 16S rRNA gene. Taxonomy was assigned using a custom database created by combining a previously established dataset of bee-associated 16S rRNA gene sequences with the SILVA NR v132 training set. Group 1=No treatment, Group 2=Vehicle pollen patty only, and Group 3=BioPatty. Hierarchal clustering of samples is shown in the dendrogram above the bar plot and was calculated using the ward.D method and "hclust" function in R. Cluster 1=Grey, Cluster 2=Red, Cluster 3=Blue.

FIG. 3A shows a Principle Component Analysis (PCA) plot of adult honey bee gut microbiota samples. Sequence variants were collapsed at genus-level identification, with CLR-transformed Aitchison distances used as input values for PCA analysis. Distance between individual samples (points) represent differences in microbiota composition, with 45.9% of variance explained by the first two principle components shown. Strength of association for genera are depicted by the length of the red arrows. Clustering of samples was determined using the "k-means" function in R. FIGS. 3B-3C show qPCR-based quantification of dominant microbiota phylotypes and *Escherichia coli* in adult nurse bee gut samples. Data represents the median (line in box), IQR (box) and minimum/maximum (whiskers) of 10 individual gut samples with duplicate technical repeats. Statistical analysis shown for one-way ANOVA with Benjamini and Hochberg corrected multiple comparisons. ns=not significant. *p<0.05, p<0.01, *p<0.001.

FIG. 4A shows growth curves of *P. larvae* in MY media supplemented with cell-free supernatant from lactobacilli strains of interest. FIG. 4B shows the percent maximal growth as determined from growth curve data ($OD_{600}$) at 48 h using the area under the curve for *P. larvae* grown in MY media supplemented with CFS from the specified lactobacilli. Data are depicted as means±standard deviation (one-way ANOVA with Dunnett's multiple comparisons) of n=3 biological replicates performed with duplicate technical repeats. FIG. 4C shows zone of inhibition measurements, which represent the mean±standard deviation radius clearance (minus the disk) on a *P. larvae* lawn grown on MY agar. Experiments were performed in biological triplicate (n=3 for each group) with technical duplicates. Statistical analysis is shown for one-way ANOVA with Dunnett's multiple comparisons made against 30 µg oxytetracycline. *Enterobacter hormaechei* B0003, *Paenibacillus illinoisensis* B0004, *Hafnia paralvei* B0008, and *Lactobacillus apis* B0011 represent isolates previously obtained from a healthy hive. FIG. 4D shows Lp39 (short rod-shaped) and *P. larvae* (long rod-shaped) were incubated in nutrient-limited media for 60 min and subsequently stained with cell permeable (4',6-diamidino-2-phenylindole; DAPI) and non-permeable (SYTOX Green) nucleic acid markers, as well as Texas Red-WGA which selectively binds to the surface of gram-positive bacteria. Cells were visualized using a Nikon Eclipse Ti2 confocal microscope. Increased uptake of SYTOX Green indicates reduced cell viability based on plasma membrane integrity. Yellow arrow points *P. larvae*, white arrow points to Lp39. Bacterial cells that were incubated with 70% ethanol (EtOH) served as a positive control to validate the assay. Scale bar=20 µM. ns=not significant, p<0.01, *p<0.001, ****p<0.0001.

FIG. 5A shows a schematic diagram illustrating the experimental design for laboratory rearing of honey bee larvae and infection timeline. FIG. 5B shows survival curves for laboratory-reared second-instar honey bee larvae that were subjected to natural infection with *P. larvae* BMR43-81 with or without 24 h pre-supplementation with LX3 delivered orally ($10^7$ CFU/mL for each strain). All statistical symbols are representative of comparisons made to respective vehicle control groups using the log-rank (Mantel-Cox; n=40 individuals for each treatment group) test.

FIG. 5C shows the pathogen load of whole honey bee larvae at day 3 post infection was determined by plating extracted homogenates on MY agar media. Colony forming units (CFU) are represented by the median with 95% confidence intervals (Kruskal-Wallis test with Dunn's multiple comparisons) shown for 10-20 individual larvae in each group as depicted by symbols on the graph. FIG. 5D shows qPCR-based quantification of dominant microbiota phylotypes and supplemental lactobacilli across treatment groups at day 3 post infection. Data represents the median (line in box) and minimum/maximum (whiskers) of 8 individual larval samples per treatment group. Statistical analysis is shown for two-way ANOVA with Tukey's multiple comparisons made against the non-infected PBS control group. nd=not detectable, ns=not significant, *p<0.05, p<0.01, *p<0.001, and ****p<0.0001.

FIG. 8A shows the differences between interindividual microbiota compositions of adult honey bee gut samples were significantly higher in Post-ABX samples in comparison to Pre-ABX samples. FIG. 8B shows the BioPatty, but not vehicle patty, supplementation for 28 days significantly reduced interindividual differences in microbiota composition following antibiotic exposure. Statistical analysis shown for Kruskal-Wallis with Benjamin Hochberg multiple comparisons. n=6 individuals from separate hives. p>0.01, **p>0.0001.

FIG. 9A shows Defensin-1 (an antimicrobial peptide involved in social immunity) was significantly increased in the BioPatty supplemented group compared to the NTC group. FIG. 9B shows that no difference was observed in Defensin-2 (an antimicrobial peptide involved in individual immunity) between the treatment groups. FIGS. 9C-D show that *Hymenoptacein* and *Apismin* (highly expressed antimicrobial peptides involved in resistance to bacterial infection) was significantly upregulated in both vehicle-treated and BioPatty groups compared to the NTC group. Statistical analysis shown for one-way ANOVA with Holm-Sidak's comparisons. n=8 individuals. *p<0.05.

FIG. 10A shows that Defensin-1 (an antimicrobial peptide involved in social immunity) was significantly increased in the BioPatty supplemented group compared to the NTC group. FIG. 10B shows that no difference was observed in Defensin-2 (an antimicrobial peptide involved in individual immunity) between the treatment groups. FIGS. 10C-D show that *Apismin* but not *Hymenoptacein* (highly expressed antimicrobial peptides involved in resistance to bacterial infection) was significantly upregulated in the BioPatty group compared to the NTC group. Statistical analysis shown for one-way ANOVA with Holm-Sidak's comparisons. n=8 individuals. *p<0.05, **p<0.01.

FIG. 11 shows a list of primers used for qPCR-based quantification of bacteria in honey bee larvae and adult gut samples.

FIG. 12 shows a list of primers used for RT-qPCR of immune-related gene expression changes during *P. larvae* infection in laboratory-reared honey bee larvae. All primer sequences presented 5' to 3'. Forward Sequences are SEQ ID NO 1: GCACGTGAAGATCTAGCAGCTC; SEQ ID NO 2: AATTATTTGGTCGCTGGAATTG; SEQ ID NO 3: TTGCTCTGTAAGGTTGTTTTGC; SEQ ID NO 4: CACGGATACATCCTGCAGTCATC; SEQ ID NO 5: TGCGCTGCTAACTGTCTCAG; SEQ ID NO 6: GCAACTACCGCCTTTACGTC; SEQ ID NO 7: AGATGGCATGCATTTGTTGA; SEQ ID NO 8: CTCTTCTGTGCCGTTGCATA; SEQ ID NO 9: GCAAACGAGATTTCAATGGCAATCTTCAG; SEQ ID NO 10: TGAGCAAAATCGTTGCTGTC; SEQ ID NO 11: GAAATGTTGAATACATCGATATTCACCGTAC; SEQ ID NO 12: ATCCTGGCCAAGTGCAGCTTC. Reverse Sequences are SEQ ID NO 13: GCACCTTCTCCTTCACCTTCAG; SEQ ID NO 14: TAACGTCCAGCAGAATGTGGTA; SEQ ID NO 15: TGTCTGGTTAACTACAAATCCTTCTG; SEQ ID NO 16: GAGAATGACGAGATACAGAACTGTCAC; SEQ ID NO 17: AATGGCACTTAACCGAAACG; SEQ ID NO 18: GGGTAACGTGCGACGTTTTA; SEQ ID NO 19: CCACGCTCGTCTTCTTTAGG; SEQ ID NO 20: CGTCTCCTGTCATTCCATT; SEQ ID NO 21: CACATTGGTAATTGTATAGTACGTTCGCATC; SEQ ID NO 22: AACGACATCCACGTTCGATT; SEQ ID NO 23: CTCCATTCCACGTAGAGGAAGTATGTC; SEQ ID NO 24: CAGCTCCTTCAATTGGATCAGCAAC.

INCORPORATION BY REFERENCE

Figure 1A:
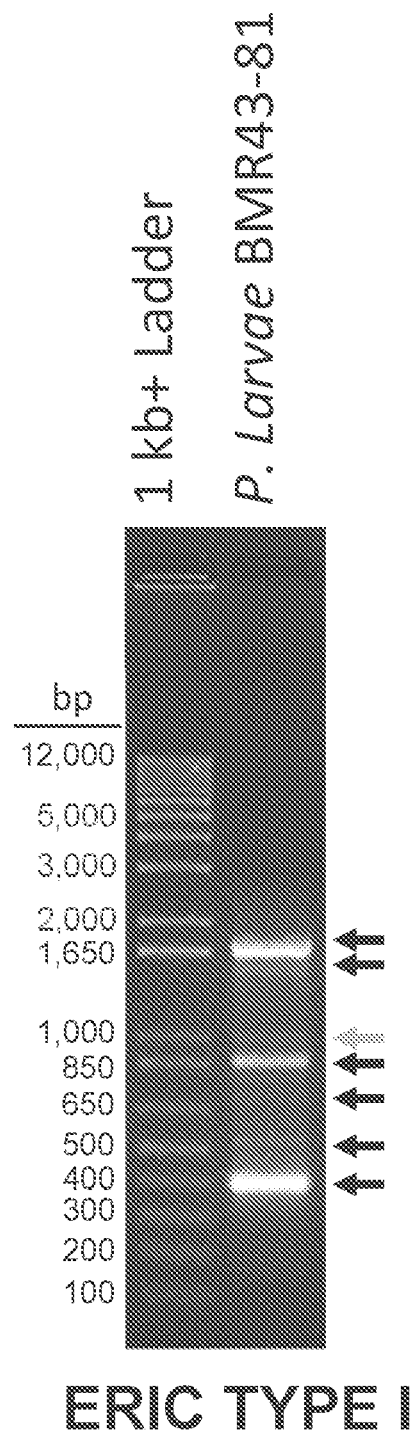
FIGS. 1A-E show retrospective analysis of BioPatty supplementation following natural AFB outbreak.

All publications, patents, and patent applications mentioned in this specification are herein incorporated by reference to the same extent as if each individual publication, patent, or patent application was specifically and individually indicated to be incorporated by reference.

DETAILED DESCRIPTION

The present disclosure is directed to providing honeybees with a probiotic composition that aids in the detoxification of neonicotinoids and inhibition of the causative agent of American foulbrood, *Paenibacillus larvae*.

Managed honey bees (*Apis mellifera*) perform critical pollination services to many agricultural crops and contribute an estimated $225 billion USD annually to the global economy. However, the health of this insect species is an ongoing concern, as illustrated by persistent population decline over the last decade. The causal factors precipitating this decline likely include a combination of pesticide exposure, infectious disease, and loss of habitat.

One pathogen that can afflict honey bee brood is the spore-forming bacterium *Paenibacillus larvae*, which causes American foulbrood (AFB). This highly adapted pathogen infects *A. mellifera* during early development and can kill brood through secretion of secondary metabolites (that have antimicrobial properties to counter microbial competitors) and chitin-degrading enzymes (enabling degradation of the peritrophic matrix) that allow breaching of the midgut epithelium, invasion of the hemocoel, and decomposition of the larva to a ropy mass. *P. larvae* strains are classified into four genotypes (ERIC I-IV) by repetitive element PCR (rep-PCR) using enterobacterial repetitive intergenic consensus (ERIC) primers. ERIC I and II are considered the most important genotypes to combat, given that they are the two most commonly associated with AFB in recent years. ERIC I isolates of *P. larvae* are most common and predicted to produce more secondary metabolites and fewer virulence factors with a 100% lethality index of 10-12 days, whereas ERIC II-IV isolates require only 6-7 days to kill infected honey bee larvae.

Although measures to control AFB in apiaries can include antibiotic treatment, selective breeding for hygienic behavior, application of bioactive essential oils, bacteriophage therapy, and administration of synthetic indoles to inhibit germination of *P. larvae*, these measures are often ineffective, and hives remain vulnerable to AFB.

*P. larvae* infection is the most widespread and destructive of the bee brood diseases. Young larvae less than 24 hours old are most susceptible to infection. Infected larvae normally die after their cell is sealed. The vegetative form of the bacterium will die but not before it produces many millions of spores. Each dead larva may contain as many as 100 million spores. This disease only affects the bee larvae but is highly infectious and deadly to bee brood, infected larvae darken and die.

Various antibiotics and antimicrobial products are available for treating American foulbrood. Antibiotics, in non-resistant strains of the pathogen, can prevent the vegetative state of the bacterium forming. Drug treatment to prevent the American foulbrood spores from successfully germinating and proliferating is possible using, e.g., oxytetracycline hydrochloride (Terramycin) and tylosin tartrate. Unfortunately, such broad-spectrum antibiotics kill beneficial bacteria as well as *P. larvae*. Moreover, the pathogenic bacteria can build a tolerance to such antibiotics. Additionally, pollen patties, widely used for feeding bee colonies during active times, can serve as an unintentionally suitable environment for the growth of *P. larvae*, spreading the infection.

While common microbial pathogens are a major threats to honey bees, sublethal doses of pesticide may enhance their deleterious effects on honey bee larvae and adults. Honey bees are suffering from elevated colony losses in the northern hemisphere possibly because of a variety of emergent microbial pathogens, with which pesticides may interact to exacerbate their impacts. For example, both honey bees and bumble bees prefer sugar solutions laced with the neonicotinoids imidacloprid, clothianidin, and thiamethoxam over pure sugar water, presumably due to the nicotine-like addition.

Sub-lethal doses of neonicotinoids have been shown to negatively impact the health of honeybees. Understanding the effects of neonicotinoid insecticides on bees is vital because of reported declines in bee diversity and distribution and the crucial role bees have as pollinators in ecosystems and agriculture. Pollinators perform sophisticated behaviors' while foraging that require them to learn and remember floral traits associated with food. Neonicotinoid pesticides, at levels shown to occur in the wild, interfere with the learning circuits in the bee's brain. Pesticides have a direct impact on pollinator brain physiology. Disruption in this important function has profound implications for honeybee colony survival, because bees that cannot learn will not be able to find food.

Canola is becoming a favored crop in the prairies, with over a million acres (1700 square miles) to be planted in North Dakota alone this year. Bayer CropScience grows hybrid canola seed in Canada, and in an ironic twist, is thereby the largest renter of honey bee pollination services in Canada, and is thus highly motivated to ensure that the product does not harm bees. Virtually all canola seed is treated with clothianidin or its precursor, thiamethoxam.

There is a growing body of science directly implicating neonicotinoid (neonic) pesticides in the significant decline of bees and other pollinators due to their detrimental effect on pollinators. Pollinator decline has been found on every continent in the world, and hundreds of pollinator species are on the verge of extinction. Since 2006, bees in the U.S. have been dying off or seemingly abandoning their hives—a phenomenon referred to as Colony Collapse Disorder. While there are many contributors to pollinator decline, two of the most important are the loss of habitat and the introduction and expansion of use of new pesticides on agricultural cropland. A specific concern centers on neonicotinoids, a relatively new class of systemic insecticides, often applied as a seed coating in commodity agriculture.

Neonicotinoids came into wide use in the early 2000s. Unlike older pesticides that evaporate or disperse shortly after application, neonicotinoids are systemic poisons. Applied to the soil or doused on seeds, neonicotinoid insecticides incorporate themselves into plant tissues, turning the plant itself into a tiny poison factory emitting toxin from its roots, leaves, stems, pollen, and nectar. As the name suggest, neonicotinoids are similar in structure to nicotine and paralyze or disorient insects by blocking a pathway that transmits nerve impulses in the insect's central nervous system.

Neonicotinoids are used to control a wide variety of insects. The first neonicotinoid, imidacloprid (Admire), became available in the United States in 1994 and is currently present in over 400 products on the market. Other neonic insecticides include acetamiprid, clothianidin, dinotefuran, nitenpyram, thiacloprid, and thiamethoxam. In 2006, neonicotinoids accounted for over 17 percent of the global insecticide market. Two of them—clothianidin and thiamethoxam-dominate the global market for insecticidal seed treatments and are used to coat the seeds of most of the annual crops planted around the world. In fact, more than 94 percent of the corn and more than 30 percent of the soy planted in the United States is pretreated with neonicotinoids.

The introduction of neonicotinoids into the agricultural marketplace occurred around the same time as the introduction of GMO crops in the mid-to-late 1990s. Monsanto and Syngenta, the undisputed leaders in patented genetically engineered seeds, also have close relationships with the leading global neonic producer, Bayer. Most new commodity crops are increasingly coming to farmers with stacked traits, which means more than one transgenic alteration. These genetically engineered and transplanted traits are marketed to farmers as providing benefits such as resistance to multiple herbicides, pests, funguses, heat and drought.

Seed treatment applications are prophylactic, meaning they are used whether or not there is any evidence of pest pressures. At least 30 percent of soybean seeds planted annually (approximately 22.5 million out of 75 million acres) are pretreated with neonic insecticides (two of the primary four being imidacloprid and thiamethoxam).

Death is not the only outcome of pesticide exposure. Sub-lethal doses of neonicotinoids can disrupt pollinators' cognitive abilities, communication and physiology. Neonicotinoids also have harmful synergistic impacts on pollinators in combination with other chemicals in the field, compounding their effects. Scientists have shown in multiple studies that the combined presence of neonicotinoids and some fungicides can increase the potency of neonicotinoids by more than 1,000-fold. In addition to their toxicity, neonicotinoids persist in plants much longer than most other insecticides, thereby compounding their impact on pollinators. They can reside in plant tissues for over a year, and some can persist for even longer in the soil. This means pollinators and other animals are exposed to the chemicals for extended periods of time and in some regions year-round.

Disclosed herein are compositions and methods of using the same to promote the health of honeybees and reduce occurrence of American foulbrood and Colony Collapse Disorder. In some embodiments, the compositions and methods provided herein can help sustain bee survival despite its exposure to insecticides, such as neonicotinoids, which are believed to be at least partially responsible for the recent demise of honey bee populations. The compositions include *Lactobacillus* probiotic bacterial strains, a sugar source, and an acceptable carrier. In some embodiments, the compositions comprise one or more *Lactobacillus* probiotic bacterial strains and a buffering agent.

Probiotic Compositions

Probiotic compositions that boost bees' immune response and normal microbiota are a desirable alternative, as they work naturally and are less likely to result in pest resistance. Embodiments of the present disclosure comprise at least one strain of *Lactobacillus*. In some embodiments, the compositions and methods disclosed herein comprise at least one of *Lactobacillus* sp. JNU 8829, *Lactobacillus acidophilus*

KU41, *Lactobacillus acidophilus* M23, *Lactobacillus brevis* CH7, *Lactobacillus casei* MB3, *Lactobacillus fermentum* NS2, *Lactobacillus plantarum* M13, *Lactobacillus plantarum* NS3, *Lactobacillus sakei* CH8, *Lactobacillus sakei* MA9, *Lactobacillus rhamnosus* GG, *Lactobacillus acidophilus* NCFM, *Lactobacillus casei* Shirota, *Lactobacillus reuteri* MM53, *Lactobacillus casei* CRL431, *Lactobacillus rhamousus* GR-1, *Lactobacillus fermentum* RC-14, *Lactobacillus rhamnosus* ATCC 53103, *Lactobacillus acidophilus* ATCC-4495, *Lactobacillus plantarum* NRRL B-4496, *Lactobacillus casei* Lcr35, *Lactobacillus casei* 01, *Lactobacillus casei* IMV B-7280, *Lactobacillus delbrueckii* subsp. *bulgaricus* 8481, *Lactobacillus brevis* KB290, *Lactobacillus brevis* CD2, *Lactobacillus johnsonii* MH-68, *Lactobacillus johnsonii* F0421, *Lactobacillus johnsonii* EM1, *Lactobacillus fermentum* ATCC 11739, *Lactobacillus fermentum* NCIMB 5221, *Lactobacillus reuteri* NCIMB 30242, *Lactobacillus reuteri* ATCC 55730, *Lactobacillus reuteri* DSM 17938, *Lactobacillus plantarum* Lp39, *Lactobacillus kunkeei* BR 1.

The compositions and methods provided herein can include one or more strains of *Lactobacillus*, such as *Lactobacillus rhamnosus* GR-1 and LGR-1, to promote pesticide detoxification. In some embodiments, the one or more strains of *Lactobacillus* provided herein may allow for the detoxification of heavy metals, agriculturally-important fungal toxins, and a variety of commonly-used pesticides.

In some embodiments, the compositions and methods provided herein include one or more strains of *Lactobacillus*, such as *Lactobacillus plantarum* Lp39, to provide beneficial immune stimulation and pathogen resistance to bees. For example, in some embodiments, the compositions and methods provided herein include one or more strains of *Lactobacillus* to mitigate neonicotinoid-induced immunosuppression and increase bee survival.

In some embodiments, the compositions and methods provided herein include one or more strains of *Lactobacillus*, such as *Lactobacillus* kunkeei BR-1 (LkBR-1), to contribute to microbiome restoration.

Formulations Compositions of the disclosure can be formulated for administration and/or use in honey bee keeping. In some embodiments, the compositions are formulated into a pollen patty. As used herein, the term "pollen patty" refers to a solid or semi-solid feeding source for honey bees which contains both a protein source and a sugar source. As used herein, "BioPatty" is a pollen patty including one or more *Lactobacillus* species. A food substance may be both a protein source and a sugar source. A protein source is understood to be a food substance containing a substantial amount of amino acids, peptides, and/or proteins suitable for consumption and metabolism by honey bees. For example, non-limiting examples of protein sources are soy flour, yeast, yeast-extract, pollen, wheast, and combinations thereof. Additionally, amino acids can be added to a pollen patty or food source in addition to, or in place of, a protein source. Non-limiting examples of suitable amino acids are arginine, histidine, isoleucine, leucine, lysine, methionine, phenylalanine, threonine, trypotophane, tryptophan, and valine, and combinations thereof. A sugar or carbohydrate source is understood to be a food substance containing a substantial amount of simple and/or complex carbohydrates suitable for consumption and metabolism by honey bees. For example, non-limiting examples of sugar sources are sugar syrup, cane sugar, beet sugar, corn syrup, honey, malt, glucose, fructose, sucrose, trehalose, maltose, and/or melezitose, and combinations thereof. The terms sugar source and carbohydrate source are herein used interchangeably unless specified otherwise. In some embodiments, a pollen patty or food source includes more than one protein source and/or more than one sugar source. In some embodiments, a pollen patty or food source includes more than one protein source and one sugar source. In some embodiments, a pollen patty or food source includes one protein source and more than one sugar source.

In some embodiments, any of the formulations disclosed herein may include additional ingredients selected from vitamins, co-factors, minerals, essential oils, micronutrients, sugars, gelatin or other gelling agents. Other added ingredients may include bee antibiotics and antifungals, including without limitation, oxytetracycline, tylosin tartrate, lincomycin hydrochloride, Terramycin®, fluvalinate, fumagillin, and combinations of these and/or other antibiotic/antifungals that are presently available. In some embodiments, a pollen patty or food source includes further nutritional sources, for example vitamins, fat sources (such as oils), yeast extracts, and/or micronutrients. For example non-limiting examples of additional nutritional sources vegetable oil (e.g. cotton seed oil, soy bean oil), Torula yeast, Brewer's yeast, vitamin B complex (e.g. thiamine, riboflavin, nicotinamide, pyridoxine, pantothenate, folic acid, and biotin), vitamin C, sodium, potassium, calcium, magnesium, chlorine, phosphorus, iron, copper, iodine, manganese, cobalt, zinc, nickel. In some embodiments, a pollen patty or food source includes a preservative.

In some embodiments, one or more compounds of the present disclosure can be combined with one or more carriers, antioxidants, and/or preservatives to provide a formulation. Exemplary carriers include oils; polymers (e.g., polyethylene glycol, polymethacrylates, ethylene-vinyl acetate copolymers, poly(acrylic acid), polyolefins (e.g., polypropylene), silicones, lactic and glycolic acid-based polymers, and copolymers thereof); microcapsules (e.g., silica microcapsules); glasses; gels; ceramics; and waxes.

Exemplary oils to use with the one or more compounds of the present disclosure include, but are not limited to, oils derived from plants such as vegetable oils and nut oils, or non-plant derived oils such as mineral oils. The oils include saturated, monounsaturated, and polyunsaturated fatty acids that are soluble in many compositions, especially the less polar or non-polar ones.

Exemplary preservatives include, for example, sorbic acid and its salts, benzoic acid and its salts, calcium propionate, sodium nitrite, sulfites (sulfur dioxide, sodium bisulfite, potassium hydrogen sulfite, etc.) and disodium ethylenediaminetetraacetic acid (EDTA). Other exemplary preservatives include ethanol and methylchloroisothiazolinone, salt, sugar, vinegar, alcohol, diatomaceous earth and castor oil, citric and ascorbic acids, vitamin C, and vitamin E.

Exemplary antioxidants include, but are not limited to, tocopherols (e.g., I-tocopherol, gamma-tocopherol, etc.), ascorbic acid, as well as synthetic antioxidants such as propyl gallate, tertiary butylhydroquinone, butylated hydroxytoluene (BHT), butylated hydroxyanisole (BHA), phenolic alcohols, flavonoids, catechins, related molecules thereof, and anthocyanins and their glycosides. The antioxidants can be soluble in most of the compositions and can react efficiently with oxygen in the dispensing systems, and therefore offer a way to decrease oxidation, breakdown, and polymerization of the formulation. In some embodiments, the oxidant can also be a preservative.

While representative carriers, preservatives, and antioxidants have been listed above, it is to be appreciated that other carriers, preservatives, and antioxidants not specifically listed above can also be used.

In some embodiments, the compositions are formulated as a pollen patty. A non-limiting example of a pollen patty includes 0.6% [v/v] phosphate buffered saline (0.137 M sodium chloride [NaCl], 0.0027 M potassium chloride [KCl], 0.01 M disodium phosphate [Na$_2$HPO$_4$], and 0.0018 M monopotassium phosphate [KH$_2$PO$_4$]; pH=7.4), 2:1 [w/v] sucrose-based simple syrup, Debittered and inactivated brewer's yeast, Granulated sucrose, Soy flour, 1×10$^8$+10% CFU *Lactobacillus rhamnosus* GR-1 per 100 g final weight (wet weight), 1×10$^8$+10% CFU *Lactobacillus plantarum* 39 per 100 g final weight. 2×10$^8$+10% CFU *Lactobacillus* kunkeei BR-1 per 100 g final weight. In some embodiments, a pollen patty includes one or more protein sources, one or more sugar sources, and a 1:1:2 ratio of *Lactobacillus rhamnosus* GR-1, *Lactobacillus plantarum* 39, and *Lactobacillus* kunkeei BR-1 per 100 g final weight. In some embodiments, a pollen patty includes a 1:1:2 ratio of *Lactobacillus rhamnosus* GR-1, *Lactobacillus plantarum* 39, and *Lactobacillus* kunkeei BR-1 per 100 g final weight.

In some embodiments, the pollen patty further includes additional protein sources, additional sugar sources, and/or additional excipients. One or more *Lactobacillus* strains can be added to other pollen patty compositions. For example, any disclosed amount of *Lactobacillus* discussed herein can be added to a pollen patty including soy flour, Torula yeast, irradiated pollen, pollard, vegetable oil, multivitamin mix, and irradiated honey or malt. In another example, any disclosed amount of *Lactobacillus* discussed herein can be added to a pollen patty including soy flour, Torula yeast or Brewer's yeast, pollard, vegetable oil, vitamin mix, irradiated honey or malt. An additional example, any disclosed amount of *Lactobacillus* discussed herein can be added to a pollen patty includes sugar syrup, granulated table sugar, soy flour, yeast, and pollen.

In some embodiments, the compositions are formulated as an isotonic solution. In some embodiments, one or more strains of *Lactobacillus* are dissolved in an isotonic solutions. Isotonic solutions include, for example, phosphate buffered saline (PBS) (e.g., 0.137 M sodium chloride [NaCl], 0.0027 M potassium chloride [KCl], 0.01 M disodium phosphate [Na$_2$HPO$_4$], and 0.0018 M monopotassium phosphate [KH$_2$PO$_4$]; pH=7.4), normal saline (90% w/v NaCl), Tris buffered saline (TBS), TBS+NaCl (e.g. TNT), phosphate-citrate buffer, cacodylate buffer, HEPES, MES, MOPS, Sørensen's phosphate buffer, or combinations thereof. In some embodiments, a liquid solution includes a 1:1:1 ratio of *Lactobacillus rhamnosus* GR-1, *Lactobacillus plantarum* 39, and *Lactobacillus* kunkeei BR-1. In some embodiments, a liquid solution includes 1:1:2 ratio of *Lactobacillus rhamnosus* GR-1, *Lactobacillus plantarum* 39, and *Lactobacillus* kunkeei BR-1.

In some embodiments, a *Lactobacillus* isotonic solution can be administered via a spray bottle with misting capability. In some embodiments, a *Lactobacillus* isotonic solution can be kept in liquid form and materials, tools, or pollen patties can be dipped or coated with the liquid composition. In some embodiments, a *Lactobacillus* isotonic solution can be administered to honey bees as a bi-weekly treatment (2 mL total volume applied to each side of each frame) throughout the active season. In some non-limiting examples, a *Lactobacillus* isotonic solution can be administered every other day, every three days, every four days, every five days, every six days, every seven days, every 8 days, every 9 days, every 10 days, every 11 days, every 12 days, every 13 days, every 14 days, every 15 days every 16 days, every 17 days, every 18 days, every 19 days, or every 20 days. In some embodiments, a *Lactobacillus* isotonic spray is used once a month, twice a month, three times a month, four times a month or more. In some embodiments, a *Lactobacillus* isotonic solution is used in regular intervals (e.g. every 10 days or according to a schedule). In some embodiments, a *Lactobacillus* isotonic solution is used in a random or unordered method. In some embodiments, a *Lactobacillus* isotonic solution is used to prepare a bee colony enclosure for use in a season. In some embodiments, a *Lactobacillus* isotonic solution is used to preserve the safety or quality of a bee colony enclosure or beekeeping tools between seasons.

Amounts of strains of interest as listed above are approximate, as one of ordinary skill in the art would understand is possible in growth of bacterial strains from batch to batch. An "effective amount" as used herein is an amount of the composition that includes an amount of one or more bacterial strains effective in treating or preventing disease in honey bees as described herein. Such an amount of the one or more bacterial strains includes any appropriate amount of a composition comprising one or more bacterial strains as described herein that can be administered to honey bees. For example, in some embodiments, 1×10^9 CFU/mL of each *Lactobacillus* bacterial strain is used. In some embodiments, 1×10^6 CFU/mL, 1×10^7 CFU/mL. 1×10^8 CFU/mL, 1×10^10 CFU/mL, 1×10^11 CFU/mL, or 1×10^12 CFU/mL of each bacterial strain are used.

An effective amount of each *Lactobacillus* strain, in any of the disclosed formulations herein, can be any of the approximate amounts disclosed herein. For example, each *Lactobacillus* strain can include 0.5×10^6 CFU/mL±20%, 1×10^6 CFU/mL±20%, 2×10^6 CFU/mL±20%, 3×10^6 CFU/mL±20%, 4×10^6 CFU/mL±20%, 5×10^6 CFU/mL±20%, 6×10^6 CFU/mL±20%, 7×10^6 CFU/mL±20%, 8×10^6 CFU/mL±20%, 9×10^6 CFU/mL±20%, 0.5×10^7 CFU/mL±20%, 1×10^7 CFU/mL±20%, 2×10^7 CFU/mL±20%, 3×10^7 CFU/mL±20%, 4×10^7 CFU/mL±20%, 5×10^7 CFU/mL±20%, 6×10^7 CFU/mL±20%, 7×10^7 CFU/mL±20%, 8×10^7 CFU/mL±20%, 9×10^7 CFU/mL±20%, 0.5×10^8 CFU/mL±20%, 1×10^8 CFU/mL±20%, 2×10^8 CFU/mL±20%, 3×10^8 CFU/mL±20%. 4×10^8 CFU/mL±20%, 5×10^8 CFU/mL±20%, 6×10^8 CFU/mL±20%, 7×10^8 CFU/mL±20%, 8×10^8 CFU/mL±20%, 9×10^8 CFU/mL±20%, 0.5×10^9 CFU/mL±20%, 1×10^9 CFU/mL±20%, 2×10^9 CFU/mL±20%, 3×10^9 CFU/mL±20%, 4×10^9 CFU/mL±20%, 5×10^9 CFU/mL±20%. 6×10^9 CFU/mL±20%, 7×10^9 CFU/mL±20%, 8×10^9 CFU/mL±20%, 9×10^9 CFU/mL±20%, 0.5×10^10 CFU/mL±20%, 1×10^10 CFU/mL±20%, 2×10^10 CFU/mL±20%, 3×10^10 CFU/mL±20%, 4×10^10 CFU/mL±20%, 5×10^10 CFU/mL±20%, 6×10^10 CFU/mL±20%, 7×10^10 CFU/mL±20%, 8×10^10 CFU/mL±20%, 9×10^10 CFU/mL±20%, 0.5×10^11 CFU/mL±20%, 1×10^11 CFU/mL±20%, 2×10^11 CFU/mL±20%, 3×10^11 CFU/mL±20%, 4×10^11 CFU/mL±20%, 5×10^11 CFU/mL±20%, 6×10^11 CFU/mL±20%, 7×10^11 CFU/mL±20%, 8×10^11 CFU/mL±20%, 9×10^11 CFU/mL±20%, 0.5×10^12 CFU/mL±20%, 1×10^12 CFU/mL±20%, or 2×10^11 CFU/mL±20%, 3×10^12 CFU/mL±20%, 4×10^12 CFU/mL±20%, 5×10^12 CFU/mL±20%, 6×10^12 CFU/mL±20%, 7×10^12 CFU/mL±20%, 8×10^12 CFU/mL±20%, 9×10^12 CFU/mL±20%. The amounts provided herein can also occur in more precise approximate amounts, including, but not limited to ±19%, ±18%, ±17%, ±16%, ±15%, ±14%, ±13%, ±12%, ±11%, ±10%, ±9%, ±8%, ±7%, ±6%, ±5%, ±4%, ±3%, ±2%, or ±1%.

Each *Lactobacillus* strain can be included, in any of the formulations disclosed herein, in a range. For example, the effective amount of each *Lactobacillus* strain can be included in the amount of $0.5\times10^6$ CFU/mL to $1\times10^{12}$ CFU/mL, $1\times10^6$ CFU/mL to $1\times10^{12}$ CFU/mL, $1\times10^7$ CFU/mL to $1\times10^{12}$ CFU/mL, $1\times10^8$ CFU/mL to $1\times10^{12}$ CFU/mL, $1\times10^9$ CFU/mL to $1\times10^{12}$ CFU/mL. $1\times10^{10}$ CFU/mL to $1\times10^{12}$ CFU/mL, $1\times10^{11}$ CFU/mL to $1\times10^{12}$ CFU/mL, $1\times10^6$ CFU/mL to $1\times10^{111}$ CFU/mL. $1\times10^6$ CFU/mL to $1\times10^{10}$ CFU/mL, $1\times10^6$ CFU/mL to $1\times10^9$ CFU/mL, $1\times10^6$ CFU/mL to $1\times10^8$ CFU/mL, $1\times10^6$ CFU/mL to $1\times10^7$ CFU/mL, $1\times10^7$ CFU/mL to $1\times10^{11}$ CFU/mL, $1\times10^7$ CFU/mL to $1\times10^{10}$ CFU/mL, $1\times10^7$ CFU/mL to $1\times10^9$ CFU/mL, $1\times10^7$ CFU/mL to $1\times10^8$ CFU/mL, $1\times10^8$ CFU/mL to $1\times10^{11}$ CFU/mL, $1\times10^8$ CFU/mL to $1\times10^{10}$ CFU/mL. $1\times10^8$ CFU/mL to $1\times10^9$ CFU/mL, or any range or sub-range within. Each *Lactobacillus* strain can be provided in the formulation in the same or similar amount(s). Each *Lactobacillus* strain can be provided in the formulation in different amounts. Two *Lactobacillus* strains can be provided in the formulation in the same or similar amount(s). In some embodiments, a ratio of 1:1:2 of *Lactobacillus rhamnosus* GR-1, *Lactobacillus plantarum* 39, and *Lactobacillus* kunkeei BR-1 is used per 100 g final weight.

The formulation can be in the form of a liquid, paste, solid, or gel. In some embodiments, the formulation is a controlled release formulation, such that the compounds can be released (i.e., volatilized) over a period of time. In some embodiments, the formulation is a controlled release formulation, such that the one or more compounds of the present disclosure contained therein can slowly release over an extended period of time (e.g., between 1 and 4 weeks, between 1 and 3 weeks, or between 1 and 2 weeks; about 1 week, about 2 weeks, about 3 weeks, or about 4 weeks). The formulation can be contained in a dispenser (e.g., a bag, a perforated tube, or an open container) that is permeable to the one or more compounds of the present disclosure. In some embodiments, the dispenser is formed of plastic, paper, wax, and/or wood.

Dosing and Methods of Administration

Some embodiments of this disclosure can be administered to honeybees as a pollen patty composition. Pollen patties can provide a means of feeding domesticated bees. The pollen patty composition may comprise pollen or a pollen substitute. In some embodiments, the pollen patty is a commercially manufactured pollen patty. In some embodiments, the pollen patty is commercially manufactured containing the probiotic composition disclosed herein. In some embodiments, the probiotic composition disclosed herein is added to a pre-made commercial pollen patty. In some embodiments, the pollen patty is created or manufactured by the end user. In some embodiments, the probiotic composition disclosed herein is added at the time the patty is made by the end user.

In some embodiments, the patty composition is placed on top of frames in the brood chamber of a domesticated honey bee hive. For example, the product can be administered as four separate treatments of 7-10 day durations at isochronous timepoints during the active season of the hive. Active season is understood by those skilled in bee-keeping and can vary based upon location. For example, in Ontario, active season is from April to October, while in California the active season can occur year-round.

Some embodiments of the disclosure can be administered as a liquid solution. In some embodiments, the liquid solution is applied using any spray bottle with misting capability. For example, the spray is administered to honey bees as treatment about once every two weeks throughout the active season. For example, about 2 mL total volume is applied to each side of each frame.

In some embodiments, a liquid solution and a pollen patty are used. In some embodiments, a liquid solution and a pollen patty are applied at the same time. In some embodiments, a liquid solution and a pollen patty are applied at different times. In some embodiments, a liquid solution is applied before addition of a pollen patty. In some embodiments, a liquid solution is applied after the addition of a pollen patty. In some embodiments, a liquid solution and a pollen patty are used during the same active season. In some embodiments, a liquid solution and a pollen patty are alternated over several active seasons. In some embodiments, a liquid solution is applied to a pollen patty.

The bee ingestible composition can be delivered to the bees in a great variety of ways. As detailed herein, bee feeding is common practice amongst bee-keepers, for providing both nutritional and other, for example, supplemental needs. Bees typically feed on honey and pollen, but have been known to ingest non-natural feeds as well. Bees can be fed various foodstuffs including, but not limited to Wheast (a dairy yeast grown on cottage cheese), soybean flour, yeast (e.g. Brewer's yeast, Torula yeast) and yeast products products-fed singly or in combination and soybean flour fed as a dry mix or moist cake inside the hive or as a dry mix in open feeders outside the hive. Also useful is sugar, or a sugar syrup. The addition of pollen to a supplement fed to bees can be used to improve palatability (e.g. 10 to 12 percent pollen), or to improve the quality and quantity of essential nutrients (e.g. 25 to 30 percent pollen) that are required by bees for vital activity.

Liquid feed can be supplied to bees inside the hive by, for example, any of the following methods: friction-top pail, combs within the brood chamber, division board feeder, Boardman feeder, etc. Dry sugar may be administered by placing a pound or two on the inverted inner cover. A supply of water should be available to bees at all times. In some embodiments, pans or trays in which floating supports-such as wood chips, cork, or plastic sponge—are present are envisaged. Detailed descriptions of supplemental feeds for bees can be found in, for example, USDA publication by Standifer, et al 1977, entitled "Supplemental Feeding of Honey Bee Colonies" (USDA, Agriculture Information Bulletin No. 413), herein incorporated by reference.

Bee Colony Enclosure

The bee colony enclosure can be any kind of an enclosed structure in which the bee colony lives and raise its young. The bee colony enclosure's internal structure can include a densely packed group of hexagonal cells, made of beeswax (i.e., a honeycomb, or a comb). The cells are used to store food (e.g., honey and pollen) and to house the brood (i.e., eggs, larvae, and pupae).

In some embodiments, the bee colony enclosure can be a naturally occurring structure occupied by bee colonies, such as hollowed-out trees. In some embodiments, the bee colony can be domestic and live in man-made beehives, which can be in an apiary. As an example, a man-made beehive can include the following parts:

(1) A hive stand on which upper hive components rest. The hive stand provides a landing board for the bees and helps to protect the bottom board from rot and cold transfer.
(2) A bottom board having an entrance for the bees to get into the hive.
(3) One or more brood boxes. The one or more brood boxes are typically the low box(es) of the hive and are where the queen bee lays her eggs. Each brood box includes brood combs, which are the beeswax structures of hexagonal cells where the queen bee lays eggs (i.e., the brood cells).

(4) Honey super box(es), which are usually shorter than the brood box, but are the uppermost box(es) where honey is stored in honeycombs. The honeycombs are the beeswax structure of hexagonal cells where the honey is stored.

(5) Frames and foundation, which are wooden or plastic frames with wax or plastic sheets with honeycomb impression where bees build wax honey combs.

(6) An inner cover, which provides separation from an overly hot or cold outer cover and can be used as a shelf for feeding or other purposes.

(7) An outer cover, which provides weather protection for the hive.

EXAMPLES

The disclosure is further described in detail by reference to the following experimental examples. These examples are provided for purposes of illustration only, and are not intended to be limiting unless otherwise specified. Thus, the disclosure should in no way be construed as being limited to the following Examples, but rather, should be construed to encompass any and all variations which become evident as a result of the teaching provided herein. Without further description, it is believed that one of ordinary skill in the art can, using the preceding description and the following illustrative examples, make and use the compounds disclosed herein and practice the claimed methods. The following working examples specifically point out various aspects and embodiments, and are not to be construed as limiting in any way the remainder of the disclosure.

Example 1. Field-Based Testing of In-Hive Patties

Field-based testing is useful to examine aspects of hive behavior and health that are challenging to model in a laboratory setting.

Compositions are prepared for use in field trials, specified below.

Composition A (Pollen Patty)

0.6% [v/v] phosphate buffered saline (0.137 M sodium chloride [NaCl], 0.0027 M potassium chloride [KCl], 0.01 M disodium phosphate [Na2HPO4], and 0.0018 M monopotassium phosphate [KH2PO4]; pH=7.4)

132.1 g±10% of 2:1 [w/v] sucrose-based simple syrup
15.4 g±10% Debittered and inactivated brewer's yeast
74.1 g±10% Granulated sucrose
28.5 g±10% Soy flour
$1 \times 10^8$ CFU±10% *Lactobacillus rhamnosus* GR-1 per 100 g final weight
$1 \times 10^8$ CFU±10% *Lactobacillus plantarum* 39 per 100 g final weight
$2 \times 10^8$ CFU±10% *Lactobacillus kunkeei* BR-1 per 100 g final weight.

The pollen patty is placed on top of frames in the brood chamber of domesticated honey bee hives. The product can be administered to honey bees as four separate treatments (7-10 days) at isochronous timepoints throughout the active season.

Composition B (Stabilized Isotonic Spray)

Phosphate buffered saline (0.137 M sodium chloride [NaCl]. 0.0027 M potassium chloride [KCl], 0.01 M disodium phosphate [Na2HPO4], and 0.0018 M monopotassium phosphate [KH2PO4]; pH=7.4)

$1 \times 10^{10}$ CFU/mL±10% *Lactobacillus rhamnosus* GR-1
$1 \times 10^{10}$ CFU/mL±10% *Lactobacillus plantarum* 39
$2 \times 10^{10}$ CFU/mL±10% *Lactobacillus kunkeei* BR-1

The liquid solution can be applied to materials and objects used in bee keeping, for example, parts of bee colony enclosures, or tools used in bee keeping Composition C (Dual-Administration Formula)

Composition C represents the concurrent administration of Compositions A and B to honey bees throughout the active season following the aforementioned treatment schedules in combination.

Initially, the three product compositions disclosed above are evaluated using the Western University research apiary (Ontario, CA). All field studies are performed in standard Langstroth-style hives and supplementation occurs on a 7-day cycle over the course of 8 weeks.

Composition A is supplemented via the lengthwise placement of the product on top of frames located in the brood-chamber, while Composition B is administered directly to each of the brood-chamber hive frames using a pump-action spray bottle and standardized number of applications per side. Composition C (dual-administration formula) is supplemented in an identical method to Composition A and B, but in combination. Primary analyses include workers' appetitive response, and the basic effects on survivorship and immune function of individual bees is recorded. Appetitive response is assessed by measuring the rate of product consumption over time (i.e., change in product weight every 3-4 days), with comparisons made to a vehicle control group supplemented with only the base pollen patty ingredients without any *Lactobacillus*. Together, the mean grams of pollen collected per day and pupal brood area on the hive frame is used as an indirect proxy of survivorship, as previous linear mixed-effect modelling has demonstrated these factors to be the best statistical predictors of colony survival (Smart M, et al., (2016) *PLOS ONE* 11(3): e0152685.). Overall hive immune function is assessed by pooling hemolymph extractions from individuals (adults and larvae) in each of the treatment groups, following by agar plate-based zone of inhibition assays against *Arthrobacter globiformis* using an established protocol (Harpur B A, et al., (2014) *PLOS ONE* 9(8): €104214.).

Additional data collected includes measurement of the hive's collective response to probiotic treatment as reflected in:

Queen brood production—Brood produced per day is measured to determine queen health status and colony reproductive capacity.

Honey production—Honey is removed from honey supers bi-weekly using standard extraction methods and subsequently weighed.

Pathogen load: Larvae, adults, beebread, and honey samples are subjected to CTAB and phenol-chloroform-based DNA extraction, followed by molecular quantification of common honey bee pathogens using real-time PCR.

Immune function: RNA is extracted from larvae and adults at different developmental points, followed by SYBR Green-based qPCR gene expression analyses of well characterized effector genes including Defensin-1, Defensin-2, *Abaecin, Apisimin*, and *Hymenoptaecin*.

Metagenomic potential of the honey bee gut microbiome is determined by performing metagenomic shotgun sequencing on adults and larvae using an Illumina® MiSeq® platform (Illumina, Inc., San Diego, CA).

Honey bee gut transcriptome is determined using an RNA-seq approach by performing whole transcriptome shotgun sequencing on larval and adult honey bee samples using the Illumina® MinION platform.

After initial safety and functionality testing, a pre-market proto-type version of each Composition is offered to provincially registered apiaries across Ontario. A typical blind experiment with consenting beekeepers is performed, which will provide useful user feedback and identify any potential issues with scaling up at a commercial level. Compositions 1-3 (BioPatty or placebo patties) is supplied to the beekeepers in series through the active season, commensurate with the size of operation. The beekeepers returns basic comparative data, including parasite load, honey yield, pollen stores and winter survivorship, in return via on-line survey.

These studies elucidate the safety and functionality of each product composition when supplemented to honey bees under realistic field-conditions. Additionally, the results demonstrate how the product affects a) productivity at the colony level b) immune function and pathogen susceptibility, and c) functional changes in the honey bee gut metagenome and transcriptome and respond to probiotic supplementation, both on an individual and colony level.

Example 2. Cage-Controlled Experiments

Composition A (herein referred to as a BioPatty) is tested in groups of n=30 same-age adult worker bees in cages, whereby treatment is replicated across multiple cages and with bees sourced from multiple donor colonies (to negate colony-level effects). Groups of workers, sampled upon eclosion from single-queen colonies (of Buckfast strain, see, e.g., Hisashi Okuyama et al., *Mitochondrial DNA* Part B, pp 338-339, online pub: 13 Mar. 2018), are fed to a standardized product consumption in cages. Subsequently, consumption is monitored over a 12-day period, as worker mature from 'nurse' to 'forager' age. Workers are monitored directly for differences in foraging activity, survivorship, and immune-gene expression against placebo controls. These data show that bees supplemented with probiotic-infused pollen patties (i) show an unreserved appetite for and consumption of the nutrient-rich patty, (ii) are as long-lived as placebo controls, and iii) show an active immune defense, as evidenced by the up-regulation of antimicrobial effector molecules upon treatment (determined by qPCR-based analyses of gene expression).

A replicated cage experiment is set up as follows. At a minimum, three biological (colonies) times three technical (cages) replicates for each BioPatty and control (for a total of 18 cages for each BioPatty formulation and for the control) are set up. The temperature is set at (32-35° C.) and the humidity of the hive from which bees is collected is measured. Thirty worker bees, sampled from designated colonies reared within the apiary at Western University, are placed in each cage along with antibiotic to simulate normal procedure, the BioPatty or control, and synthetic queen pheromone (Available from: Intko Supply Ltd. Suite 604, 3345 Kingsway, Vancouver, BC, V5R 0A7) to simulate presence of a living Queen bee. Parameters measured are appetite, weight of the BioPatty over time, survival time in the cage, and health of the bees.

In order to determine health of the bees, five bees are removed on day 7 and the rest of the bees are removed at time of death. The whole bee is then placed in liquid nitrogen, thawed, and the brain, abdomen, and gut are removed. RNEasy® (Invitrogen) is used to extract the RNA and the brain sample is screened for genes associated with immune status, including the IMD and Toll pathways, antimicrobial peptide production, and epithelial tight junction barrier proteins including ZO-1 and Claudin 3. Next, the dissected gut is processed to identify microbiota composition differences between BioPatty- and vehicle-supplemented honey bees using a metagenomic approach, as described above. This information is then used to identify pathogen-inhibiting and toxin-degrading genes important in overall host detoxification and susceptibility to a wide range of pathogens. The degree of genetic diversity is then examined, the presence of the specified *Lactobacillus* strains supplemented is confirmed, and gene presence especially relevant to host-microbe interactions is compared (using established gene-function databases that are publicly available at www.ncbi.nlm.nih.gov), in addition to biofilm formation, nutrient assimilation, pesticide breakdown, pathogen defense (against bacteria, fungi, viruses and mites) and immunity.

An additional series of experiments are done as described above, again with six cages and 30 bees per cage, but with artificial conditions simulating inducing cold stress as an additional stressor to determine how the BioPatty may help honey bees improve their ability to overwinter successfully (an environmental stressor implicated in honey bee decline).

Example 3. Bacterial Strains and Cultures

*Lactobacillus plantarum* Lp39 (Lp39; American Type Culture Collect [ATCC], number 14917), *Lactobacillus rhamnosus* GR-1 (LGR-1; ATCC number 55826), and *Lactobacillus* kunkeei BR-1 (LkBR-1; previously isolated from a healthy honey bee hive) were routinely cultured anaerobically at 37° C. using de Man, Rogosa, and Sharpe (catalog number 288130; BD Difco) broth or agar supplemented with 10 g/litre D-fructose (catalog number F-3510; Sigma-Aldrich; MRS-F), unless otherwise stated. Isolated *P. larvae* BMR43-81 (from diseased honey bee larvae in this study) was routinely cultured in a microacrophilic incubator at 37° C. under 5% $CO_2$ using modified Mueller-Hinton (2 g/liter Mueller-Hinton broth [catalog number 212322; BD Difco] and 15 g/liter yeast extract [catalog number 212750; BD Difco]; MY) broth and agar, unless otherwise stated. Honey bee isolates *Enterobacter hormaechei* B0003, *Paenibacillus illinoisensis* B0004, *Hafnia paralvei* B0008, and *Lactobacillus apis* B0011 used for inhibition assay experiments were from a geographically distinct honey bee hive exhibiting no signs of disease. Isolates *Enterobacter hormaechei* B0003, *Paenibacillus illinoisensis* B0004, *Hafnia paralvei* B0008 were cultured aerobically at 37° C. in MY, whereas *Lactobacillus apis* B0011 was cultured anaerobically at 37° C. in MRS-F.

Example 4. Apiary Set Up, Treatment Groups, and Sampling Procedure

Field trials were performed on managed Chilean-sourced honey bees (*Apis mellifera*) in an experimental apiary owned and operated through Western University (London, Ontario, Canada) for the purposes of scientific investigation. The apiary consisted of ten colonies located in a single geographic location and housed in standard Langstroth hives that were elevated approximately 36 inches above ground level using wooden support beams. Two hives were used for each of the following treatment groups: 1) a no-treatment control (NTC) group that received equal levels of physical disturbance without any form of supplementation, 2) a vehicle pollen patty group that received nutritional supplementation in the form of a 250 g patty containing standard pollen substitute ingredients (28.5 g soy flour, 74.1 g granulated sucrose, 15.4 g debittered brewer's yeast, 132.1 g of a 2:1 [w/v] simple sucrose-based syrup solution) with the addition of 4 mL vehicle (0.01 M PBS) per patty, and 3) a BioPatty group which received the 250 g base pollen patty ingredients with the additional infusion of Lp39, LGR-1, and LkBR-1 each at a final concentration $10^9$ CFU/g. Supplementation of hives occurred twice during the field trial on day 0 and day 7. Sampling of hives occurred on days 0 and 12 during which thirty adult nurse bees (located on frames with active brood) were collected from each hive. Sampling of larvae (third- to fifth-instar) occurred only on day 12 as our original intentions were not to monitor early life stages. Individuals were collected equally from each hive per treatment group. Pooling of samples occurred within the same hive and the same number of pooled samples were collected from each hive per treatment group. Colony ID was recorded but was not considered in downstream analyses in favour of preserving a more robust dataset. Following the detection of AFB on day 12, honey bees were promptly euthanized, and hives scorched according to local regulations.

Example 5. Isolation and Identification of *P. larvae* Bacterial Colonies

Standard methods for identification of American foulbrood were followed as previously described (de Graaf D C, Alippi A M, Antúnez K, Aronstein K A, Budge G, Koker D D, et al. Standard methods for American foulbrood research. *J Apic Res* 2013; 52: 1-28). Briefly, infected larvae exhibiting signs of active disease were extracted from the hive, homogenized in equal volumes 0.01 M phosphate-buffered saline (PBS; w/v) using a sterile motorized pestle, serial diluted and spread plated on MYPGP (10 g/litre Mueller-Hinton broth, 15 g/litre yeast extract, 3 g/litre $K_2HPO_4$, and 1 g/litre sodium pyruvate;), brain heart infusion (BHI; catalog number 211059; BD Difco), and MY agar. Isolated *P. larvae* colonies were visually verified on the basis of their Gram-stain and morphological characteristics, and then re-streaked to obtain pure cultures from which DNA was extracted as described previously (Daisley B A, Trinder M, McDowell T W, Collins S L, Sumarah M W, Reid G. Microbiota-mediated modulation of organophosphate insecticide toxicity by species-dependent lactobacilli interactions in a *Drosophila melanogaster* insect model. *Appl Environ Microbiol* 2018; 84: e02820-17). Universal 16S rRNA gene primers pA SEQ ID NO 25: (5'-AGAGTTT-GATCCTGGCTCAG-3') and pH SEQ ID NO 26: (5'-AAGGAGGTGATCCAGCCGCA-3') were used for PCR as previously described in Daisley et al 2018. The amplified product was then purified by 1.0% agarose gel electrophoresis, extracted with a QIAquick gel extraction kit (catalog number 28704; Qiagen), and sequenced using the aforementioned primers with the Applied Biosystems 3730 Analyzer platform at the London Regional Genomics Centre (Robarts Research Institute, London, Canada). DNA was similarly extracted from *Enterobacter hormaechei* B0003, *Paenibacillus illinoisensis* B0004, *Hafnia paralvei* B0008, and *Lactobacillus apis* B0011 isolates. The corresponding 16S rRNA partial sequences were uploaded to NCBI GenBank (accession numbers: MK618560 and MK618171-MK618174).

Example 6. Repetitive Element Sequence-Based PCR

DNA from a single colony of the *P. larvae* isolate was extracted using the InstaGene (Bio-Rad) matrix protocol following manufacturer's instructions. Genotyping of the *P. larvae* isolate was then performed using the ERICIR SEQ ID NO 27: (5'-ATGTAAGCTCCTGGGGATTCAC-3') and ERIC2 SEQ ID NO 28: (5'-AAGTAAGTGACTGGGGT-GAGCG-3') primers as previously described, for example in Versalovic J, Schneider M, Bruijn F J D, Lupski J R. Genomic fingerprinting of bacteria using repetitive sequence-based polymerase chain reaction. *Methods Mol Cell Biol* 1994; 5: 25-40. Using 10 µL of the amplified products, banding pattern was analyzed on a 0.8% agarose gel stained with ethidium bromide and visualized under UV light in an AlphaImager 2200 station (Innotech).

Example 7. qPCR-Based Quantification of Microbial Communities in Larval and Adult Honey Bee Samples Honey bee larvae (whole body) and adults (dissected whole abdomens) were surface sterilized using 0.25% sodium hypochlorite, followed by a 30 s wash in dd$H_2O$. DNA was then extracted from samples using the previously described CTAB method (Powell J E, Martinson V G, Urban-Mead K, Moran N A. Routes of acquisition of the gut microbiota of the honey bee *Apis mellifera*. *Appl Environ Microbiol* 2014; 80: 7378-7387). Bacterial loads were then determined by qPCR with the Power SYBR Green kit (Applied Biosystems) using universal and phylotype-specific 16S rRNA primers listed in FIG. 11. All qPCR reactions were performed in DNase and RNase-free 384-well microplates on a Quant Studio 5 Real-Time PCR System (Applied Biosystems) and analyzed with associated software. Copy numbers of target 16S rRNA genes were calculated as previously described using established primer efficiencies and limit of detections.

Example 8. 16S rRNA Gene Library Preparation

Targeted amplification of the 16S rRNA V4 region was performed using the established GOLAY-barcoded primers (5'-3') SEQ ID NO 29: ACACTCTTTCCCTA-CACGACGCTCTTCC-GATCTNNNNxxxxxxxxxxxxGTGCC AGCMGCCGCGGTAA and (5'-3') SEQ ID NO 30: CGGTCTCGGCATTCCTGCTGAACCG CTCTTCCGATCTNNNNxxxxxxxxxxxxGGAC-TACHVGGGTWTCTAAT wherein 'xxxxxxxxxxxx' represents the sample-specific 12-mer barcode following the Illumina adapter sequence used for downstream library construction. Utilizing a BioMek Automated Workstation (Beckman Coulter), 2 µL of sample DNA (5 ng/µL) was added to a 96-well 0.2 mL PCR plate containing 10 µL of each primer per well (3.2 pmol/µL), followed by the addition of 20 µL GoTaq 2X Colourless Master Mix (Promega). Final plates were then sealed using PCR-grade adhesive aluminum foil and placed in a Prime Thermal Cycler (Technie). PCR reaction conditions were as follows: an initial activation step at 95° C., followed by 25 cycles of 95° C. for 1 min, 52° C. for 1 min, and 72° C. for 1 min. After completion, the thermocycler was held at 4° C., and amplicons subsequently stored at −20° C. until further processing.

Example 9. 16S rRNA Sequencing and Data Analysis

Processing of amplicon libraries was conducted at the London Regional Genomics Centre (Robarts Research Institute, London, Canada) in which amplicons were quantified using PicoGreen (Quant-It; Life Technologies, Burlington, ON), pooled at equimolar ratios, and sequenced on the MiSeq paired-end Illumina platform adapted for 2×250 bp paired-end chemistry. Sequence reads were then processed, aligned, and categorized using the DADA2 (v1.8) pipeline to infer exact amplicon sequence variants (SVs) from amplicon data [32]. Briefly, sequence reads were filtered (reads truncated after a quality score of </=2 and forward/reverse reads truncated after 155/110 bases, respectively) and trimmed (10 bases off 5' end of reverse reads) using optimized parameter settings as recommended. Next, sequence reads were de-replicated, de-noised, and merged using DADA2 default parameters with read recovery rates ranging from 83.9-94.5%. Taxonomy was assigned to SVs using a customized database consisting of the SILVA non-redundant v132 training set and a previously established honey bee-specific seed alignment of 276 unique representatives. Raw sequence reads were uploaded to the NCBI Sequence Read Archive and are accessible under BioProject ID PRJNA525184.

Example 10. In Vitro Inhibition Assays for *P. Larvae*

Vegetative *P. larvae* cells were cultivated via aerobic growth in MY media at 37° C. for 48 h, followed by a 1:50 sub-culturing step, and then harvested during mid log-phase. Bacterial suspensions were then adjusted to $OD_{600}$=0.75 and spread over freshly-prepared MY agar plates (300 μL). Lactobacilli strains of interest were grown to stationary phase under their optimal growth conditions (described above). Subsequently, cells were gently centrifuged at 4,500×g and then washed twice in 0.01 M PBS, followed by resuspension in 0.01 M PBS at an adjusted concentration of $1×10^9$ cells/mL. The resultant suspensions (20 μL) were spotted onto sterile filter disks (7 mm diameter; Whatman) and placed onto MY plates freshly spread with *P. larvae*. Plates were incubated in microaerophilic conditions under 5% $CO_2$ at 37° C. and zones of inhibition measured after 48 h. Sterile 0.01 M PBS served as a negative control which showed no effect on *P. larvae* growth. All antibiotic control disks (diameter=7 mm) contained 30 μg of either tetracycline, doxycycline, or oxytetracycline hydrochloride (Oxoid; Thermo Scientific).

Inhibition of *P. larvae* growth in solution was tested with the incubation of cell-free supernatant (CFS) from Lp39, LGR-1, and LkBR-1. All bacterial strains tested were cultured in MY (with the addition of 10 g/L D-fructose for LkBR-1; blank vehicle controls for this media failed to demonstrate any inhibitory properties on *P. larvae*) under each of their aforementioned optimal growth conditions, and then were harvested in stationary phase and adjusted to $1×10^9$ CFU/mL. Subsequently, bacterial suspensions were 0.2 μM-filtered sterilized to obtain CFSs, which were then pH-adjusted (pH=6.2; original pH of media) to eliminate any non-specific influence that pH differences may have on *P. larvae* growth. Vegetative *P. larvae* cells grown acrobically at 37° C. in MY were obtained in mid log-phase as above, and then diluted to $OD_{600}$=0.1 in fresh MY media with the addition of 12.5% CFS (v/v) or 12.5%0.2 μM filtered-sterilized MY vehicle. Suspensions were then added to a 96-well U-bottom plate in 200 μL aliquots in technical triplicate prior to sealing of wells with optically clear adhesive films. Plates were incubated at 37° C. with 150 RPM orbital shaking for 48 h with $OD_{600}$ measurements taken every 30 min using a BioTek microplate reader.

Example 11. Fluorescent-Based Bacterial Cell Viability Assays

Log-phase harvested *P. larvae* and stationary-phase Lp39 were gently centrifuged at 4,500×g for 10 minutes, washed twice in 0.01 M PBS, and re-suspended in glucose supplemented Krebs-Ringer solution (120 mM NaCl, 4.9 mM KCl, 1.2 mM $MgSO_4$, 1.7 mM $KH_2PO_4$, 8.3 mM $Na_2HPO_4$, and 10 mM glucose, pH 7.3). Co-incubation of Lp39 and *P. larvae* were 1 h in duration and performed with $1×10^7$ CFU/mL of each bacteria. Following incubation, bacterial cells were stained using the ViaGram Red+ Bacterial Gram Stain and Viability Kit (Invitrogen) according to manufacturer recommendations. Subsequently, samples were sealed under a coverslip and visualized using the 60× oil-immersion lens on a Nikon Eclipse Ti2-A confocal microscope. Bacterial cells were identified on the basis of their differential morphology, with long rod-shaped bacterium representing *P. larvae* and short rod-shaped bacteria representing Lp39.

Example 12. Infection Assays Using Laboratory-Reared Honey Bee Larvae

First instar honey bee larvae were removed from ten nearby hives exhibiting no sign of disease using a Chinese grafting tool, placed in 6-well tissue culture plates containing 2.5 mL of RJb1 media (50% [w/v] royal jelly, 0.9% [w/v] yeast extract, 5.1% [w/v] D-glucose, and 5.1% [w/v] D-fructose), and then were transported to laboratory conditions in an insulated container maintained at 37° C. Individuals were then randomized without regard for their colony of origin, pooled into groups of n=40, separated into 6-well tissue culture plates containing 2.5 mL RJb1 media, and orally supplemented either LX3 ($1×10^7$ CFU/mL of each Lp39, LGR-1, and LkBR-1) or vehicle (0.01 M PBS) for 24 h prior to subsequent infection. Second instar larvae were then transferred to fresh individual wells in a 96-well flat bottom tissue culture plate containing 25 μL RJb2 media (50% [w/v] royal jelly, 1.3% [w/v] yeast extract, 6.4% [w/v] D-glucose, and 6.4% [w/v] D-fructose) with the addition of $1×10^4$ spores of *P. larvae* or vehicle (sterile dd$H_2O$). On day 1 post-infection, honey bee larvae were fed fresh RJb3 media (50% [w/v] royal jelly, 1.7% [w/v] yeast extract, 7.7% [w/v] D-glucose, and 7.7% [w/v] D-fructose) for the remainder of the experiment with incremental increases in volume of 10 μL/day with a starting diet of 25 μL on day 1. Subsequently, larvae were monitored for survival every 24 h via gentle surface agitation using a sterile pipette tip. Individuals were considered dead on the basis of an absent response to physical stimuli and the sustained lack of movement or respiration. Dead larvae were immediately removed from their well.

Example 13. TRIzol-Based RNA Extraction and qPCR for Host Gene Expression

In vitro-reared honey bee larvae were surface sterilized using 0.25% sodium hypochlorite. RNA was then extracted from whole larvae using 700 μL TRIzol (Invitrogen) following manufacturer's instructions. Quality of RNA was evaluated using a microvolume spectrophotometer (DS-11 Spectrophotometer; DeNovix) and determined to have A260/280 absorbances ratios between 1.9-2.2. cDNA was synthesized from 1,500 ng of total RNA using a High-Capacity cDNA Reverse Transcription Kit following manufacturer's instructions (Applied Biosystems, catalog number: 4368813).

Oligonucleotide primers were used for qPCR reactions and are listed in FIG. 12. Preliminary experiments identified honey bee alpha-tubulin (XM_391936) to be most stably expressed (compared to ribosomal protein S5 [XM_624081], microsomal glutathione-S-transferase [XM_394313], and UDP-glucuronyltransferase [XM_392727]) endogenous control under our specific set of experimental conditions, and thus was chosen as the internal standard for normalization as per MIQE guidelines (Bustin S A, Benes V, Garson J A, Hellemans J, Huggett J, Kubista M, et al. The MIQE guidelines: minimum information for publication of quantitative real-time PCR experiments. *Clin Chem* 2009; 55: 611-622). cDNA was diluted 10-fold and used for qPCR reactions with the Power SYBR Green kit (Applied Biosystems). All qPCR reactions were performed in DNase and RNase-free 384-well microplates using a Quant Studio 5 Real-Time PCR System (Applied Biosystems) and analyzed with associated software. Relative gene expression was calculated using the 2-44 Ct method. PCR amplification was confirmed via melt-curve dissociation analyses to verify expected product and check for non-specific amplification.

Example 14. Simultaneous Extraction of DNA Following RNA Extraction

DNA was back extracted from the TRIzol homogenates of laboratory-reared honey bee larvac (described above) using a back-extraction buffer (BEB) consisting of 4 M guanidine thiocyanate, 50 mM sodium citrate, and 1 M Tris base. Samples were diluted and then used for qPCR as described above to assess the microbial loads of major phylotypes in laboratory-reared honey bee larvae during *P. larvae* infection.

Example 15. Retrospective Analysis of BioPatty Supplementation Following Natural AFB Outbreak After 12 days of experimentation, classical signs of AFB were detected using the qualitative in-field "rope-test". This was confirmed by isolation of a non-pigmented strain of *P. larvae* from brood samples exhibiting signs of disease. Molecular identification via 16S rRNA gene sequencing, followed by a BLAST search against the GenBank Bacteria and Archaca 16S ribosomal RNA sequences database (NCBI), demonstrated the isolate to most closely match *P. larvae* strain DSM 7030 (Query cover=99%, E-value=0.0, and Identity=99.45%; NR_042947.1). Furthermore, ERIC-subtyping of the *P. larvae* isolate using rep-PCR demonstrated a banding pattern (FIG. 1A) that matched well with the previously-characterized *P. larvae* ERIC subtype I.

Figure 1B:
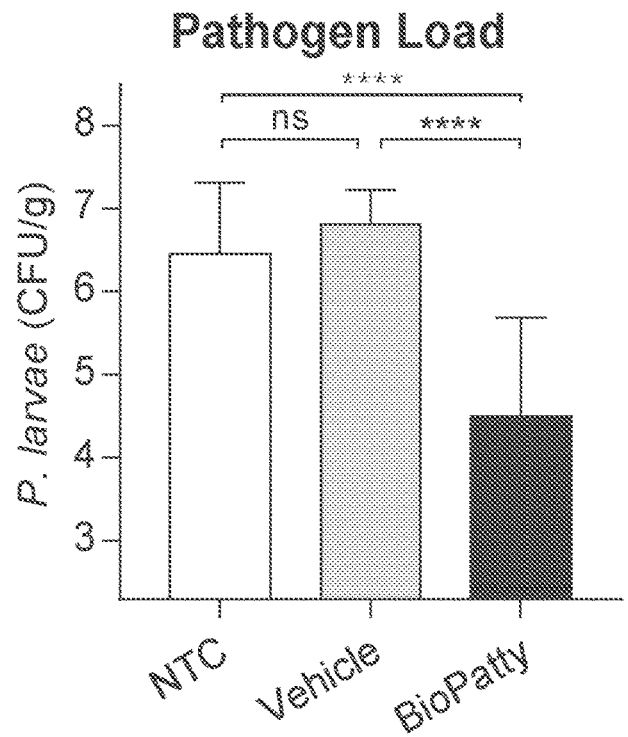

To determine differences in larval pathogen load between treatment groups, *P. larvae* abundances were enumerated in third- to fifth-instar larvae using a cultured-based method. Larvae from the BioPatty-supplemented group exhibited significantly lower pathogen loads in comparison to NTC and vehicle-supplemented groups (one-way ANOVA with Tukey's multiple comparisons, P<0.0001 for both), with no observable differences between the latter two groups (FIG. 1B).

Figure 1C:
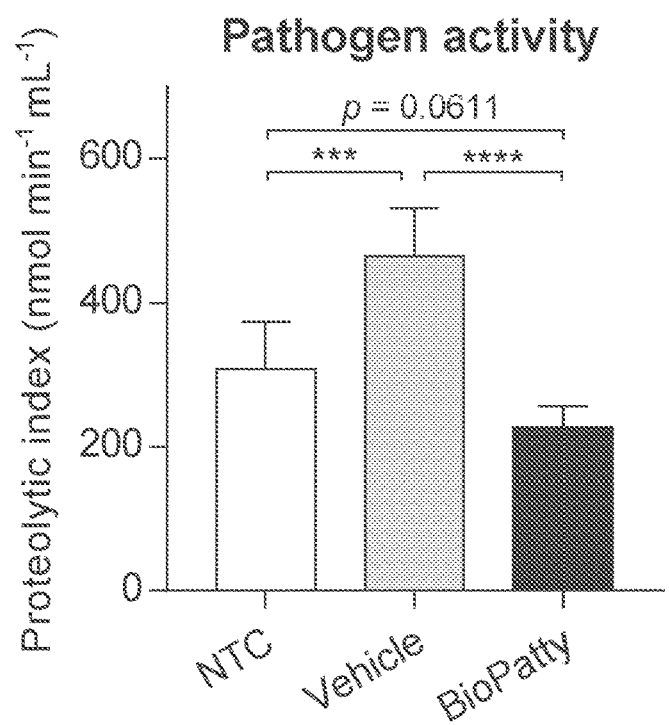

Larval samples from vehicle-supplemented groups were shown to have a significantly higher proteolytic index than samples from NTC and BioPatty-supplemented groups (one-way ANOVA with Tukey's multiple comparisons, P=0.0006 and P<0.0001, respectively; FIG. 1C). A trend towards decreased proteolytic activity was observed in the BioPatty treatment group relative to NTC (one-way ANOVA with Tukey's multiple comparisons, P=0.0611; FIG. 1C).

Figure 1D:
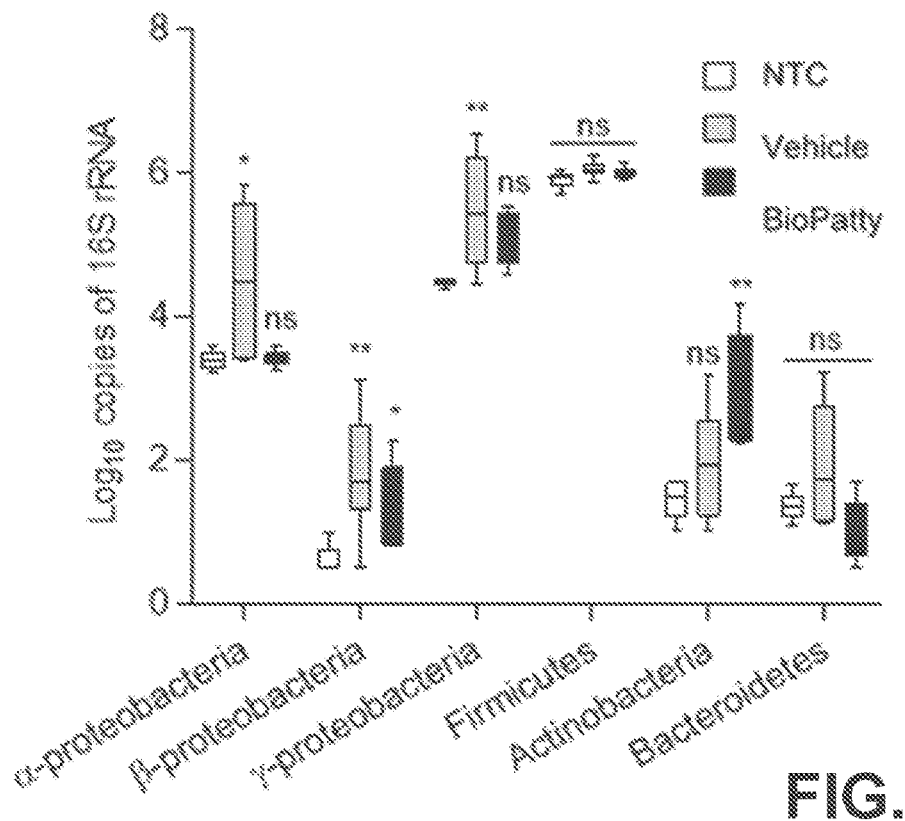
Figure 1E:
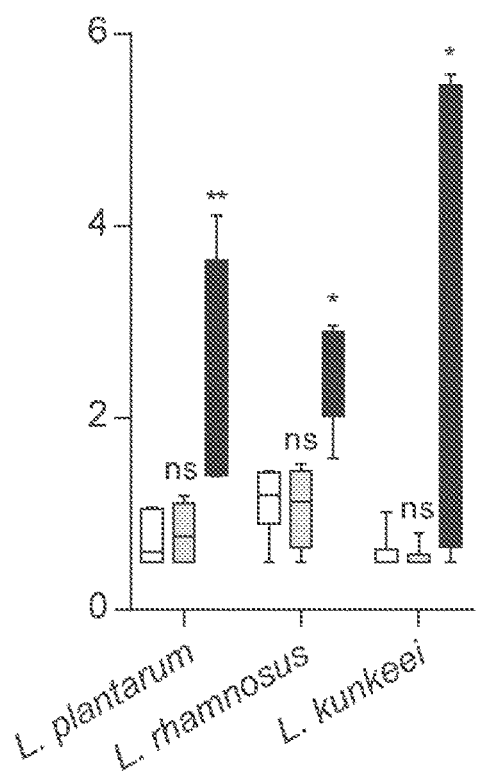

Using a qPCR-based approach to enumerate low levels of bacteria in honey bee larvae [29], the six major phylotypes commonly associated with the microbiota of honey bees were measured. Larval samples from the vehicle-supplemented group displayed significantly higher levels of Alphaproteobacteria, Betaproteobacteria, and Gammaproteobacteria (one-way ANOVA with Dunnett's multiple comparisons, P=0.0222, P=0.0084, P=0.0069, respectively) compared to the NTC group (FIG. 1D). BioPatty-supplemented larvae, by contrast, had significantly higher levels of Actinobacteria and Betaproteobacteria (one-way ANOVA with Dunnett's multiple comparisons, P=0.0026, and P=0.0431, respectively) compared to the NTC group, but no differences were found in Alphaproteobacteria and Gammaproteobacteria loads (FIG. 1D). Moreover, using species-specific primers it was found that larval samples from the BioPatty group had significantly higher levels of *L. plantarum, L. rhamnosus*, and *L. kunkeei* (Kruskal-Wallis test with Dunn's multiple comparisons, P=0.0080, P=0.0135, and P=0.0417, respectively) compared to the NTC group on day 12 of the field trial (FIG. 1E).

Example 16. Total Bacterial Loads and 16S rRNA Sequencing of the Adult Honey Bee Gut Microbiota During an AFB Outbreak Under Natural Field Conditions To further examine potential polymicrobial interactions and dynamic changes that occur in the bacterial communities associated with honey bees during the AFB outbreak, 16S rRNA gene sequencing was performed on the gut microbiota of adult worker bees. Nurse-aged adult bees were chosen for examination based on their close association with brood and previous reports demonstrating them to be good estimators of overall hive microbial diversity. After omitting control samples, the total nurse bee microbiota dataset contained 579,789 reads, ranging from 24,352 to 81,014 reads per sample. An average of 8.96% of total reads were removed from each sample following quality assurance measures using the DADA2 pipeline (Callahan B J, McMurdie P J, Holmes S P. Exact sequence variants should replace operational taxonomic units in marker-gene data analysis. *ISME J* 2017; 11: 2639-2643), leaving a total of 527,824 filtered reads. Taxonomy was assigned to SVs using a custom-designed classification database consisting of the SILVA non-redundant v132 training set and a honey-bee specific database of high-quality reference sequences (Newton I L, Roeselers G. The effect of training set on the classification of honey bee gut microbiota using the Naïve Bayesian Classifier. *BMC Microbiol* 2012; 12: 221). SVs identified as *Wolbachia* spp. or chloroplasts were removed. After implementing a 1% abundance cut off, a total of 112 unique SVs remained. A bar plot and dendrogram visually representing the relative proportions of taxa in the samples is provided in FIG. 2C. These results are consistent with past surveys demonstrating a simple and distinctive community profile in the adult honey bee gut microbiota.

Figure 2A:
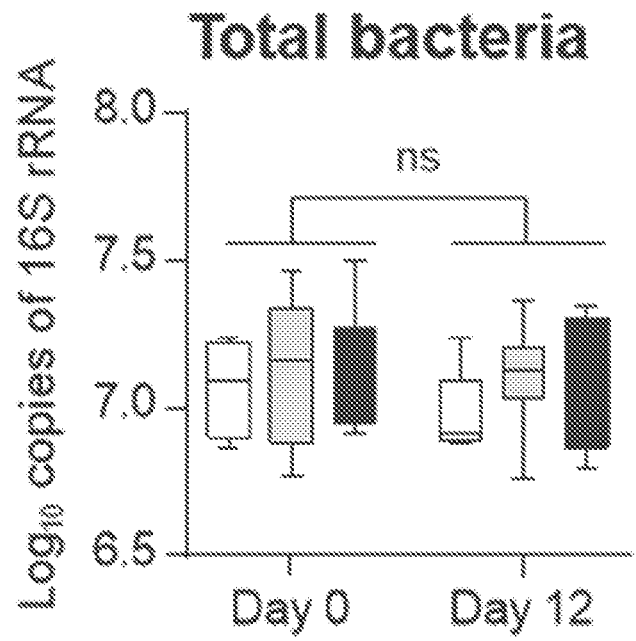
FIGS. 2A-C show total bacterial loads and 16S rRNA sequencing of the adult honey bee gut microbiota during an AFB outbreak under natural field conditions. qPCR-based quantification of total gut bacteria is shown in FIG. 2A, and the total *P. larvae* loads in surface-sterilized adult nurse bees is shown in FIG. 2B. Data represents the median (line in box) and minimum/maximum (whiskers) of 8 adult gut samples in each treatment group with duplicate technical repeats performed. Statistical analysis shown for two-way ANOVA with Tukey's multiple comparisons. ns=not significant, *p<0.05, **p<0.01.
Figure 2B:
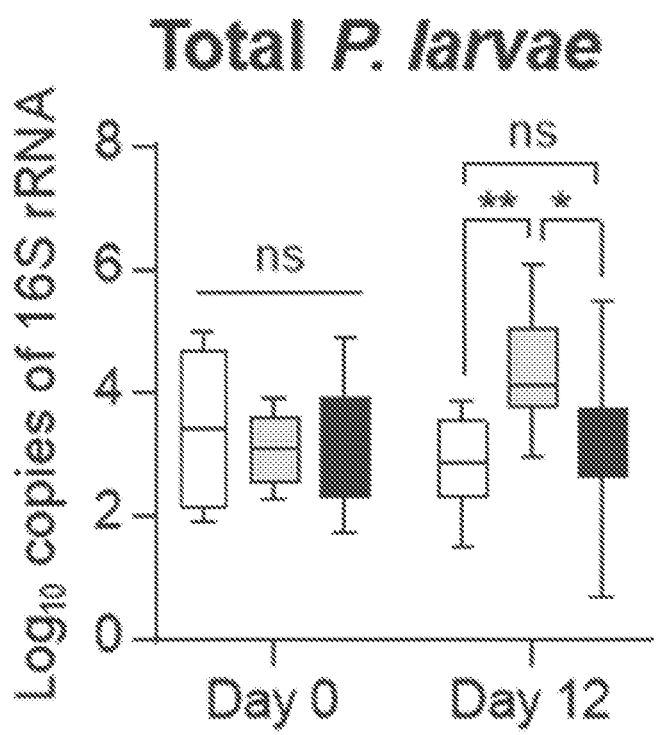
Figure 2C:
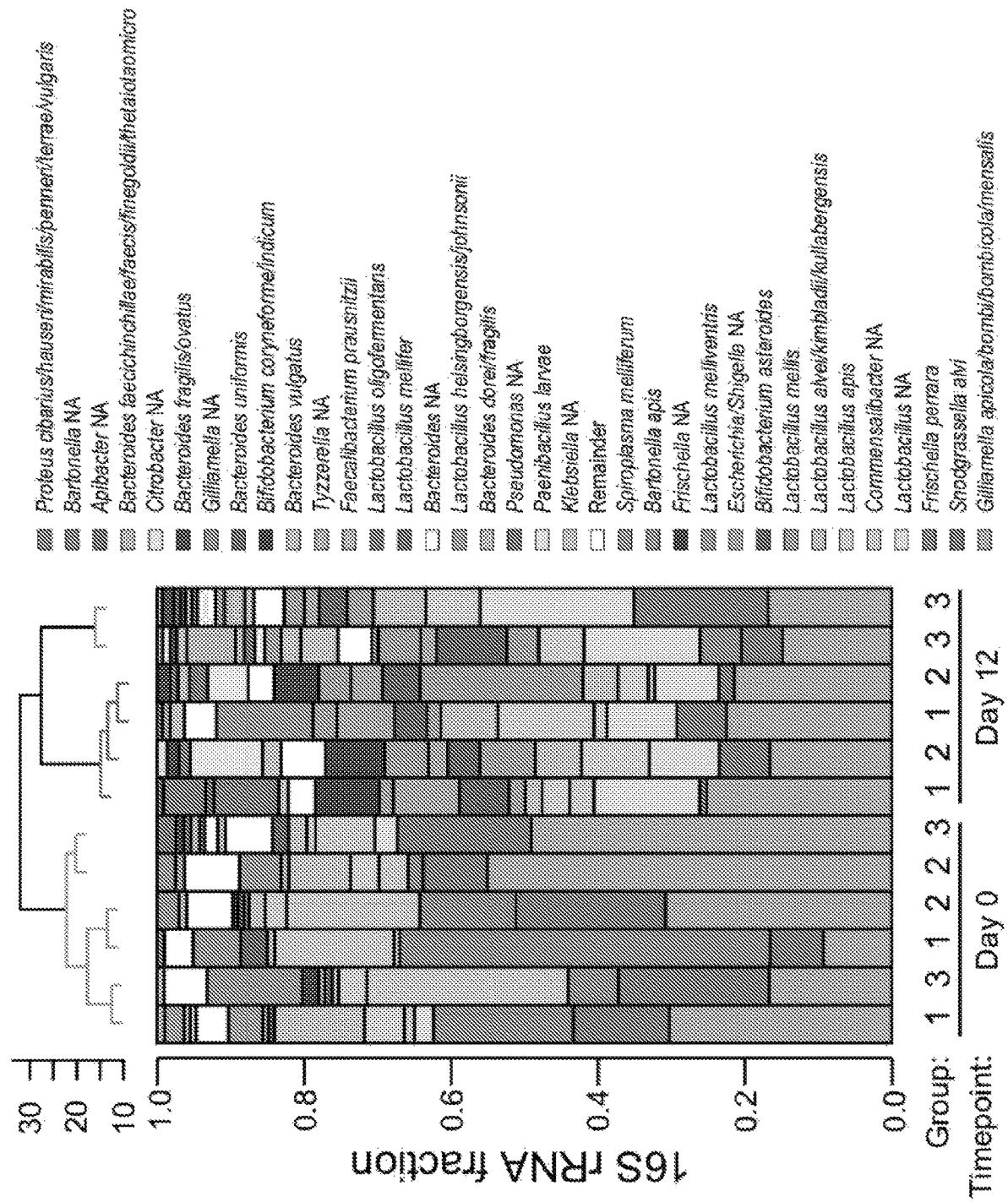

The dendrogram in FIG. 2C shows distinct clustering of samples based on time-point (day 0 vs day 12) and between samples on day 12 (NTC and vehicle-treated samples vs BioPatty samples) based on Aitchison distances, a suitable metric for the analysis of compositional data (Gloor G B, Reid G. Compositional analysis: a valid approach to analyze microbiome high-throughput sequencing data. *Can J Microbiol* 2016; 62: 692-703). No significant differences in total bacteria loads existed between any of the treatment groups at any time-point during the field trial, based on qPCR-based quantification of total bacteria load using universal 16S rRNA primers and honey bee 8-actin as a loading control (FIG. 2A). However, *P. larvae* levels in nurse bees from vehicle-treated hives were significantly higher than in NTC and BioPatty treatment groups on day 12 (two-way ANOVA with Tukey's multiple comparisons, P=0.0053 and P=0.0245, respectively; FIG. 2B).

Figure 3A:
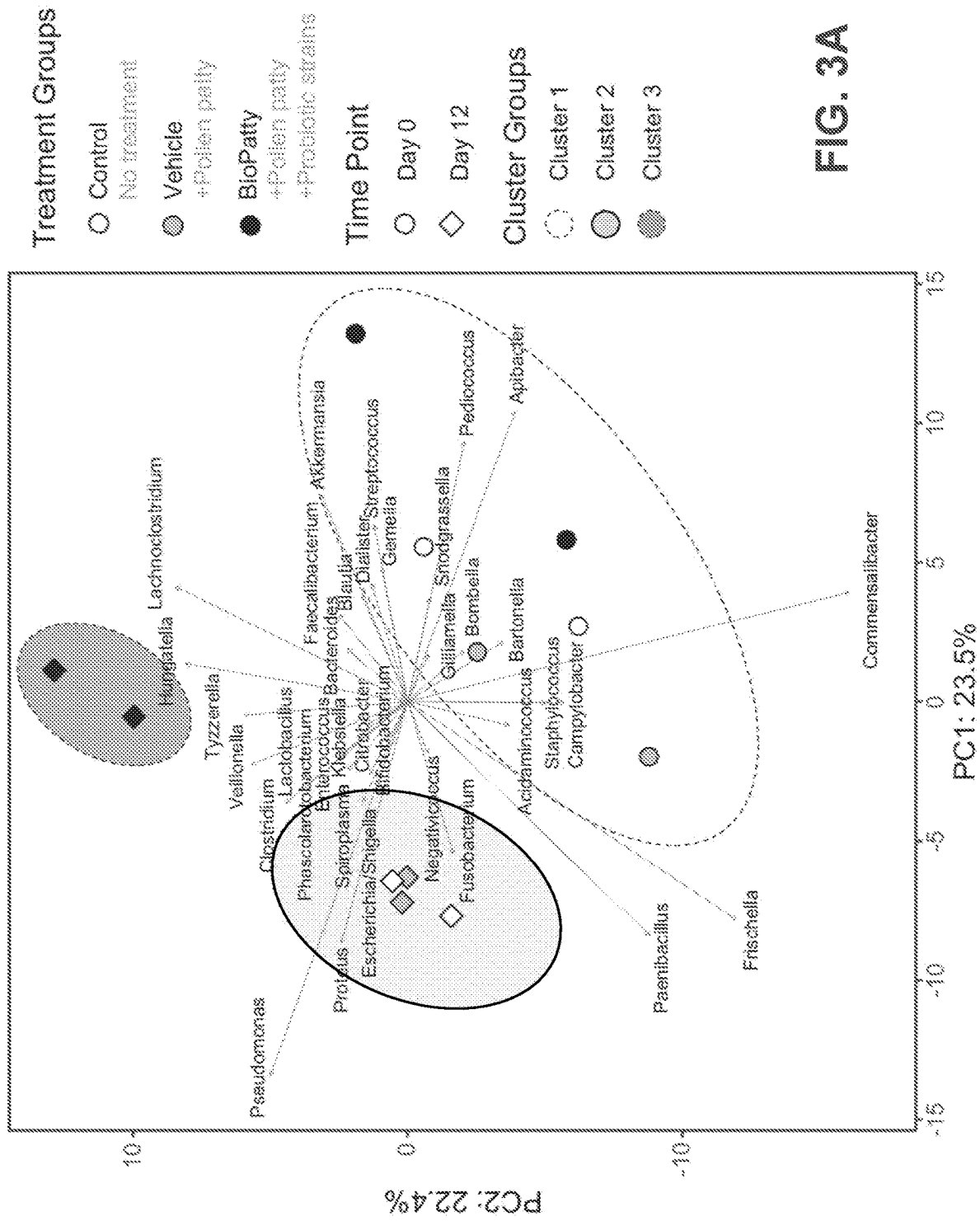
FIGS. 3A-C show results of exploratory comparison of the gut microbiota in adult nurse bees during AFB outbreak.

Example 17. Exploratory Comparison of the Gut Microbiota in Adult Nurse Bees During AFB Outbreak Using the 112 unique SVs identified, samples were centred log ratio (CLR) transformed to generate Aitchison distances, which were subsequently used to perform a principal component analysis on the nurse bee microbiota dataset (FIG. 3A). Principal components 1 and 2 explain 45.9% of the total variance in the microbiota composition between individual samples (FIG. 3A). Additionally, k-means clustering was used to partition samples into distinctive groups that had similar microbiota compositions. Three distinctive clusters were calculated and shown to be associated with both experimental time-point and treatment. The largest influencers were identified as species from *Apibacter, Commensalibacter, Frischella, Paenibacillus*, and *Pseudomonas* (strength of association depicted by arrows; FIG. 3A).

Figure 3B:
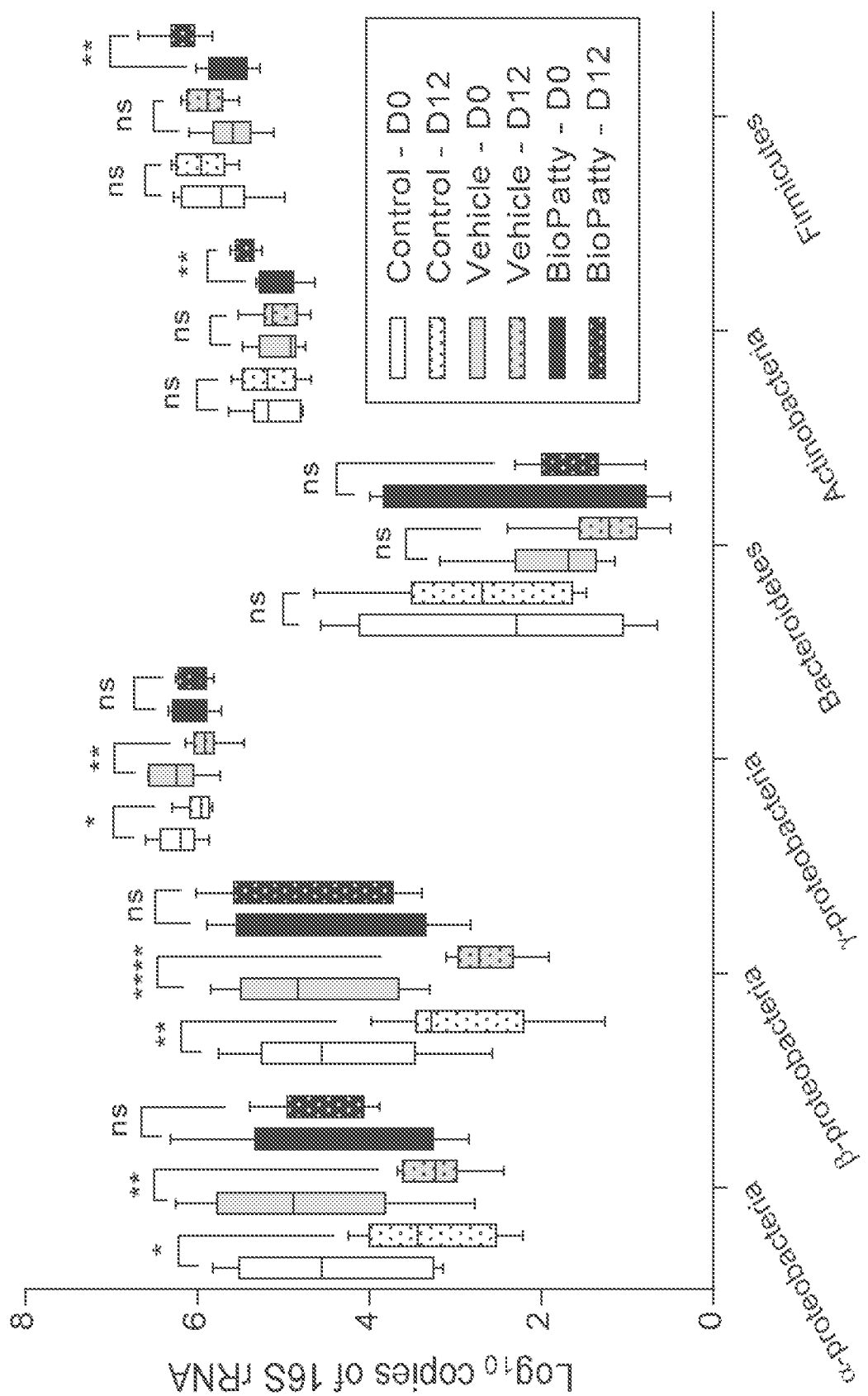
Figure 3C:
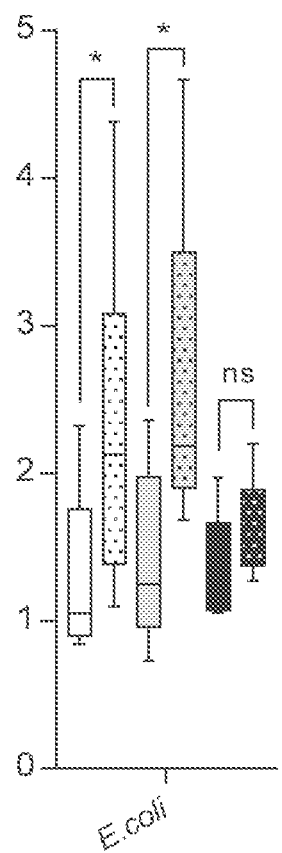

To further validate the 16S rRNA gene sequencing dataset, bacteria in the gut microbiota of adult nurse bees were quantified by qPCR using established phylotype-specific primers. NTC and vehicle-supplemented groups were found to have significantly less Alphaproteobacteria (one-way ANOVA with Benjamini and Hochberg multiple comparisons, P=0.0190, P=0.0019), Betaproteobacteria (one-way ANOVA with Benjamini and Hochberg multiple comparisons, P=0.0046, P=0.0001), and Gammaproteobacteria (one-way ANOVA with Benjamini and Hochberg multiple comparisons, P=0.0151, P=0.0029) on Day 12 (post-AFB detection) in comparison to Day 0 (pre-AFB detection; FIG. 3B). BioPatty-treated groups had higher levels of Actinobacteria and Firmicutes (one-way ANOVA with Benjamini and Hochberg multiple comparisons, P=0.0083 and P=0.0066, respectively) on Day 12 compared to Day 0 (FIG. 3B). Based on observations from the compositional dataset (FIG. 2C and FIG. 3A), *Escherichia coli* was quantified via qPCR using species-specific primers. Absolute abundance of *E. coli* in adult nurses was found to be significantly higher on Day 12 compared to Day 0 for NTC and vehicle-supplemented groups but not the BioPatty-supplemented group (one-way ANOVA with Benjamini and Hochberg multiple comparisons, P=0.0351, P=0.0217, P=0.7302, respectively; FIG. 3C).

Example 18. In Vitro Growth and Cell Viability of *Paenibacillus larvae* is Reduced by Lp39

Figure 4A:
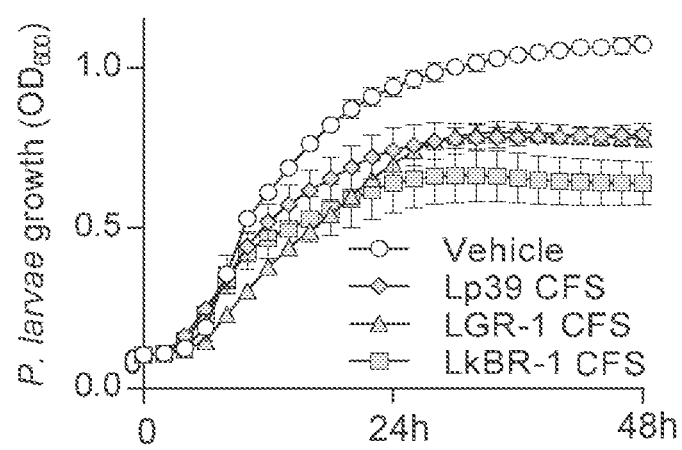
FIGS. 4A-4D shows that In vitro growth and cell viability of *Paenibacillus larvae* is reduced by Lp39.
Figure 4B:
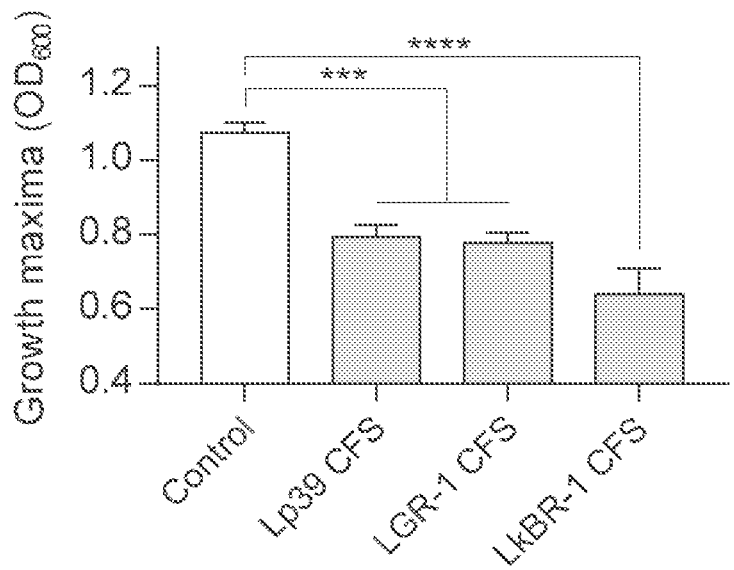
Figure 4C:
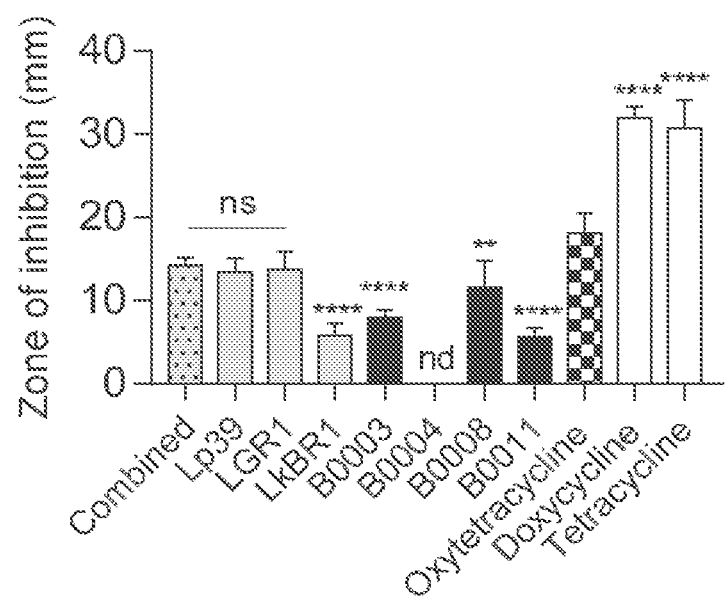

Cell-free supernatants (CFS) from stationary-phase Lp39, LGR 1, and LkBR-1 grown in MY media were tested for their ability to inhibit *P. larvae* growth in solution. Following incubation with 12.5% CFS, time-coursed measurement of *P. larvae* growth demonstrated that all lactobacilli strains negatively affected the growth maxima of *P. larvae* in solution (FIG. 4A-B). Using standard plate-based zone of inhibition assays, we tested the *P. larvae*-inhibiting properties of several common antibiotics, specific lactobacilli strains of interest, and previously derived honey bee isolates. All antibiotics and bacteria, except *Paenibacillus illinoisensis* B0004, showed some level of inhibition against *P. larvae* on solid surface growth media (FIG. 4C). Lp39, LGR-1 and the combination of Lp39, LGR-1, and LkBR-1 were as efficient as the guideline recommended antibiotic, oxytetracycline, in their ability to inhibit *P. larvae* (FIG. 4C). Other tetracycline-related antibiotics, including tetracycline itself and doxycycline, were significantly more effective at inhibiting *P. larvae* than oxytetracycline (one-way ANOVA with Dunnett's multiple comparisons, P<0.0001 for both; FIG. 4C).

Figure 4D:
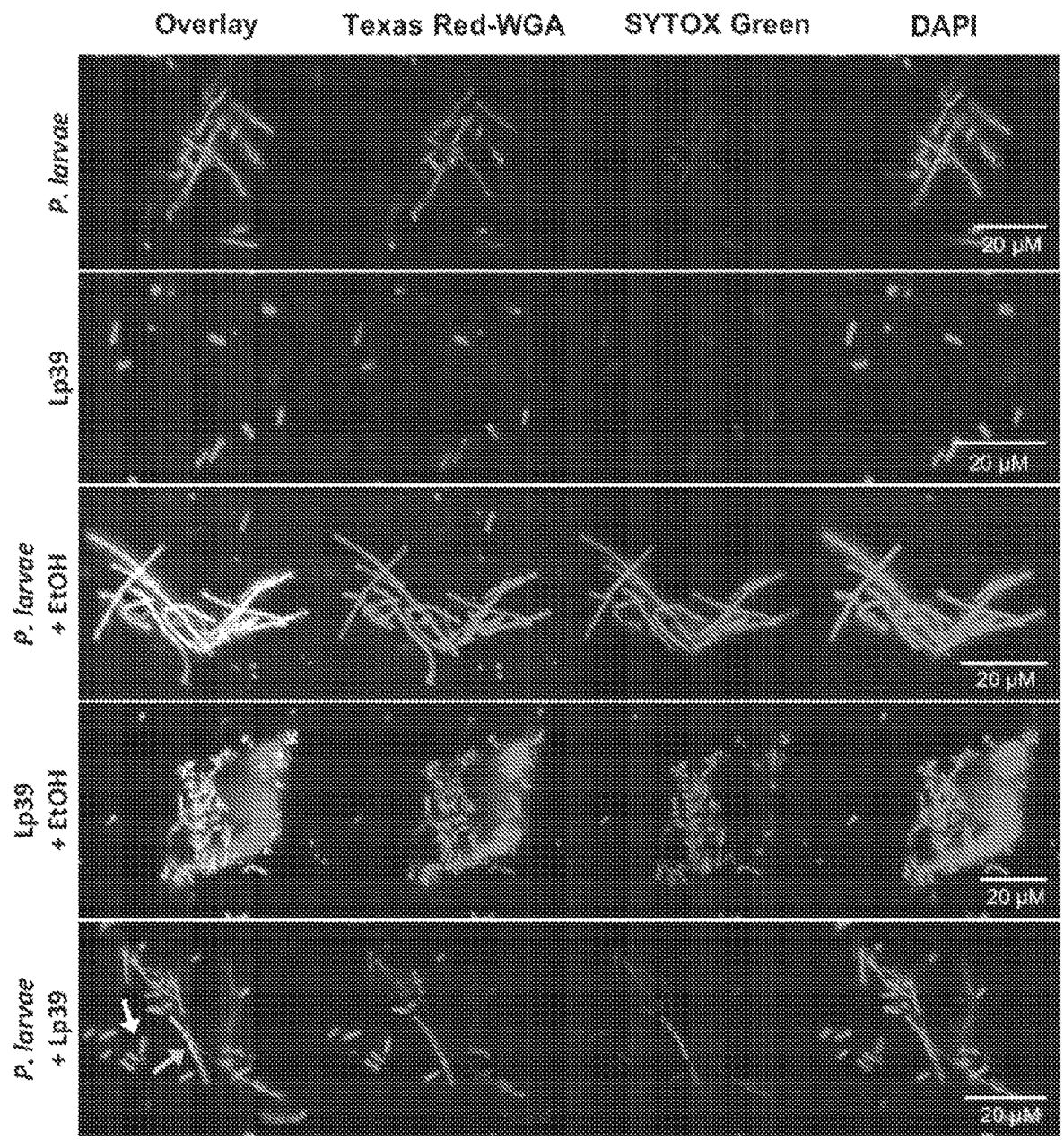

These findings compliment numerous studies demonstrating the inhibitory properties of various lactobacilli on *P. larvae* both in vitro and in vivo, however they did not explain whether the tested lactobacilli can kill *P. larvae* cells or simply inhibit their growth similar to bacteriostatic antibiotics. A fluorescent-based cytotoxicity assay on Lp39 and *P. larvae* cells demonstrated uptake of SYTOX Green in *P. larvae* cells (long and rod-shaped) but not Lp39 cells (short and rod-shaped) during co-incubation for 1 h in a glucose-supplemented physiological buffer (FIG. 4D).

Figure 5A:
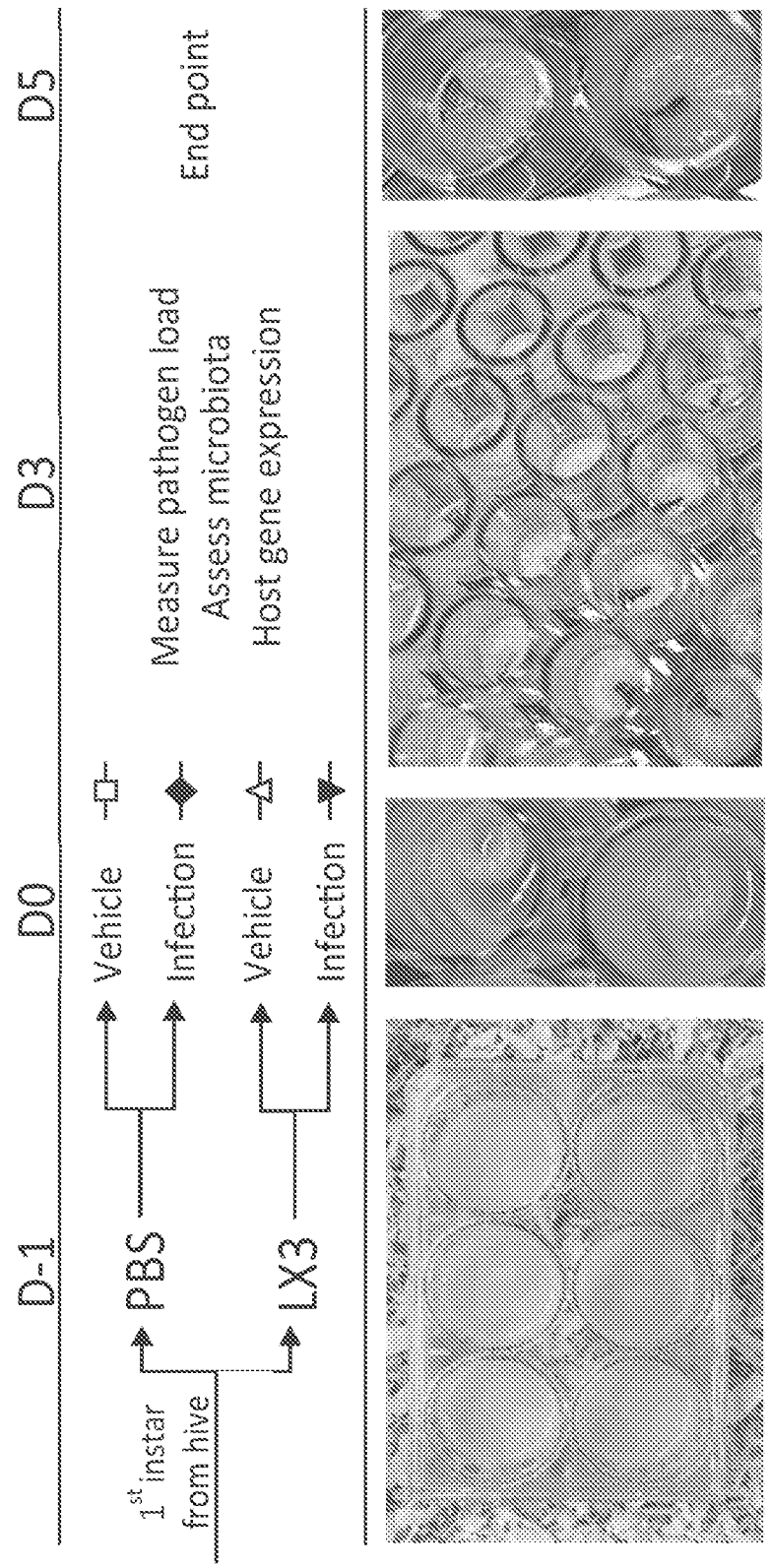
FIGS. 5A-5D show that prophylactic supplementation of Lp39, LGR-1, and LkBR-1 (LX3) improves survival during natural *P. larvae* infection.
Figure 5B:
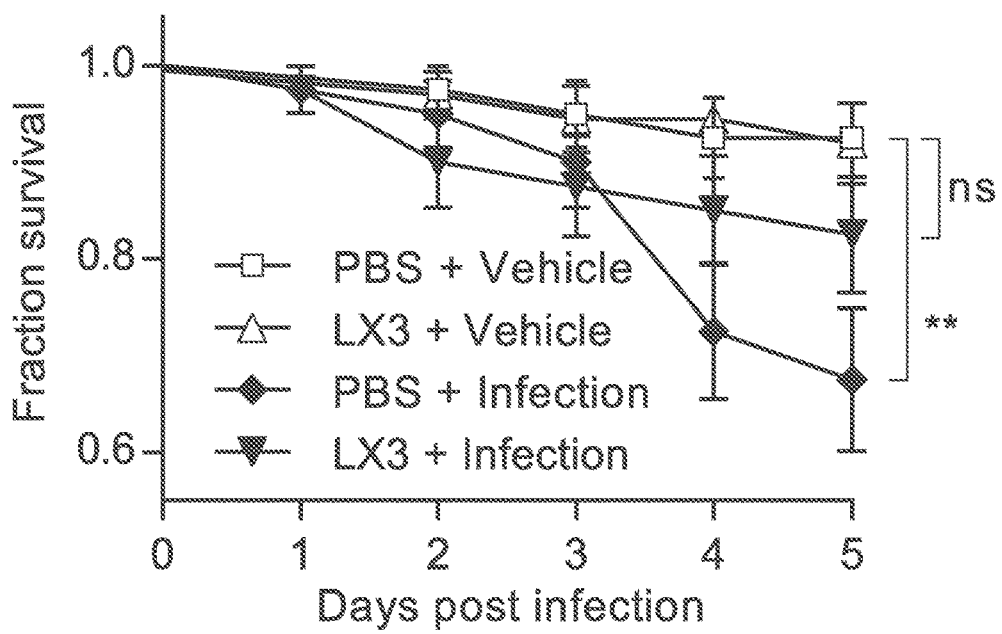
Figure 5C:
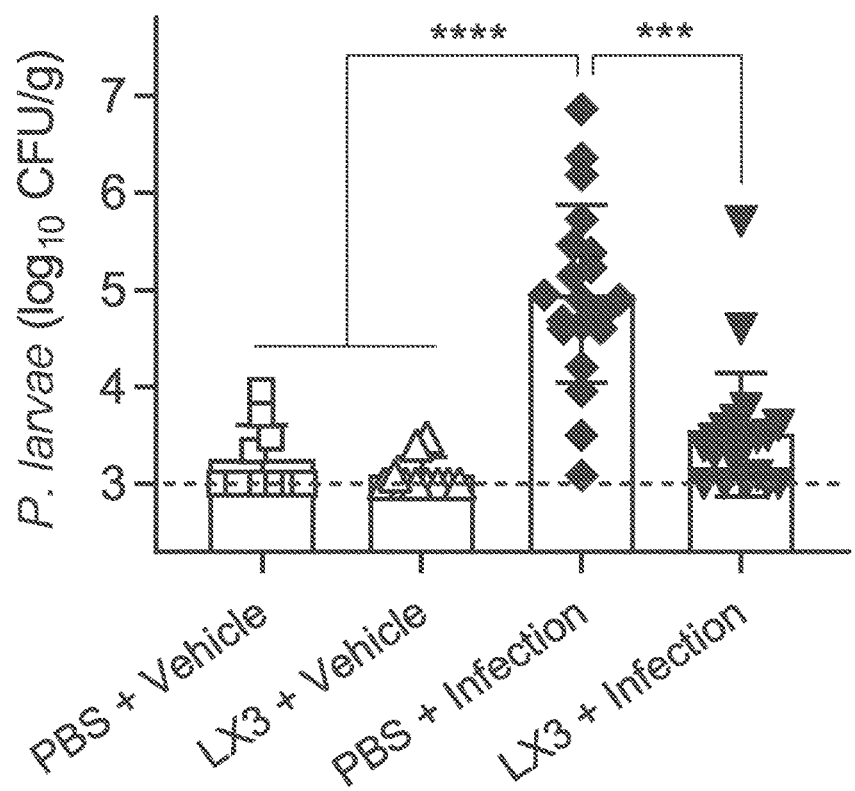

Example 19. Prophylactic Supplementation of Lp39, LGR-1, and LkBR-1 (LX3) Improves Survival During Natural *P. larvae* Infection LX3 supplementation significantly improved overall survival (log-rank [Mantel-Cox], chi-square=11.79, P=0.0081) and reduced early time-point deaths (Gehan-Breslow-Wilcoxon test, chi-square=4.462, P=0.0347) during infection compared to PBS supplemented vehicles (FIG. 5B). In addition, LX3-supplemented honey bee larvac exhibited significantly reduced levels of *P. larvae* (Kruskal-Wallis test with Dunn's multiple comparisons, P=0.0005) at 3 days post-infection compared to PBS-supplemented individuals (FIG. 5C).

Figure 5D:
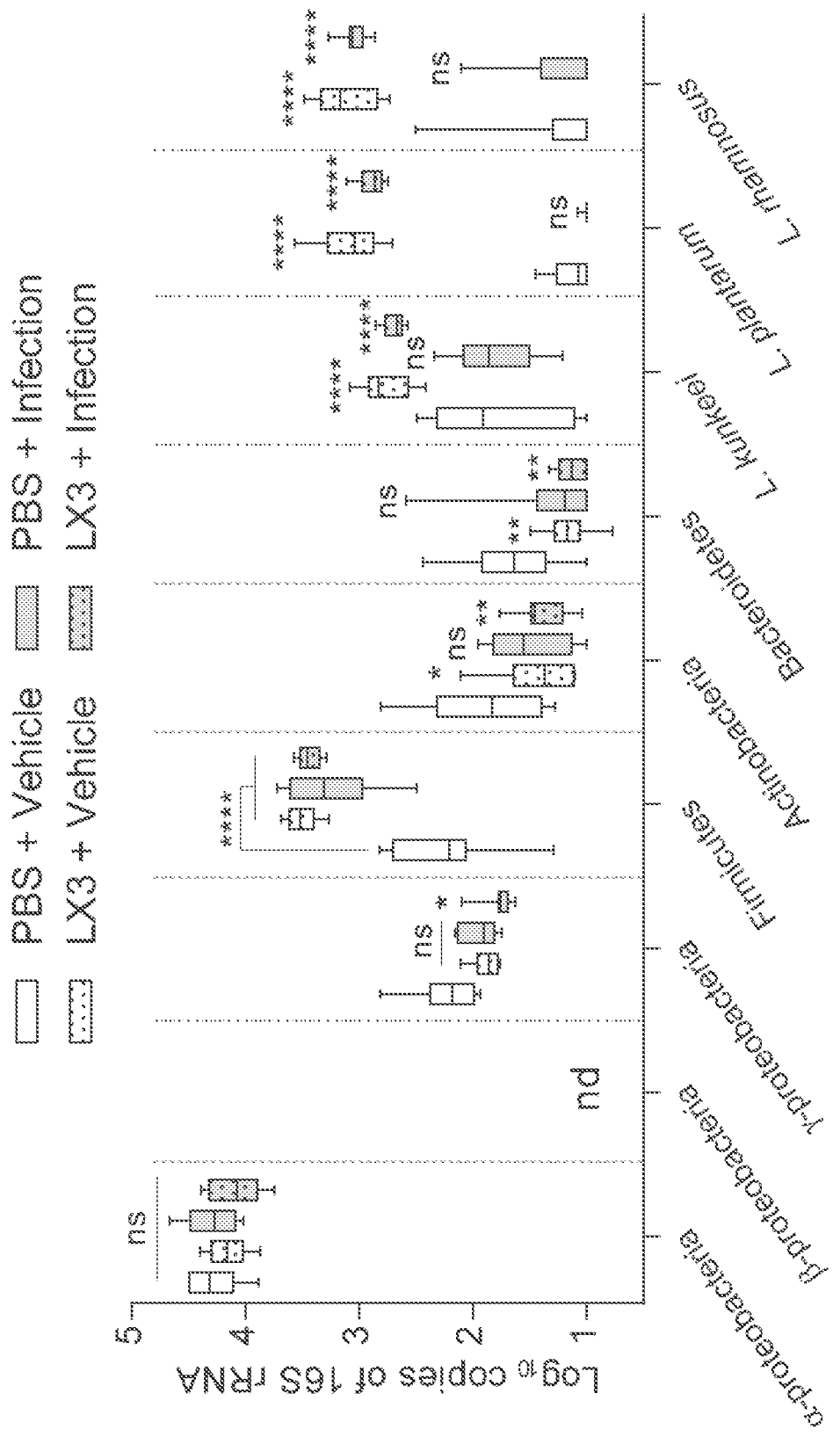

Using a qPCR-based approach to enumerate low levels of indigenous bacteria in the microbiota of in vitro-reared honey bee larvae during infection, the same six major phylotypes previously assessed in day 12 larval samples from our field-trials were measured (FIG. 1D). Under laboratory-controlled conditions, *P. larvae* infection had no significant effect on any of the phylotypes tested when compared with non-infected controls on day 3 post-infection. Infected honey bee larvae supplemented with LX3 demonstrated significantly lower levels of Gammaproteobacteria and Bacteroidetes (two-way ANOVA with Tukey's multiple comparisons, P=0.0195 and P=0.0046, respectively) compared to non-infected PBS supplemented controls (FIG. 5D). Consistent with field data, the use of species-specific primers showed that both infected and non-infected larvae supplemented LX3 had significantly higher levels of *L. plantarum, L. rhamnosus*, and *L. kunkeei* compared to infected and non-infected PBS supplemented larvae at 96 h following initial supplementation (FIG. 5D).

Figure 6:
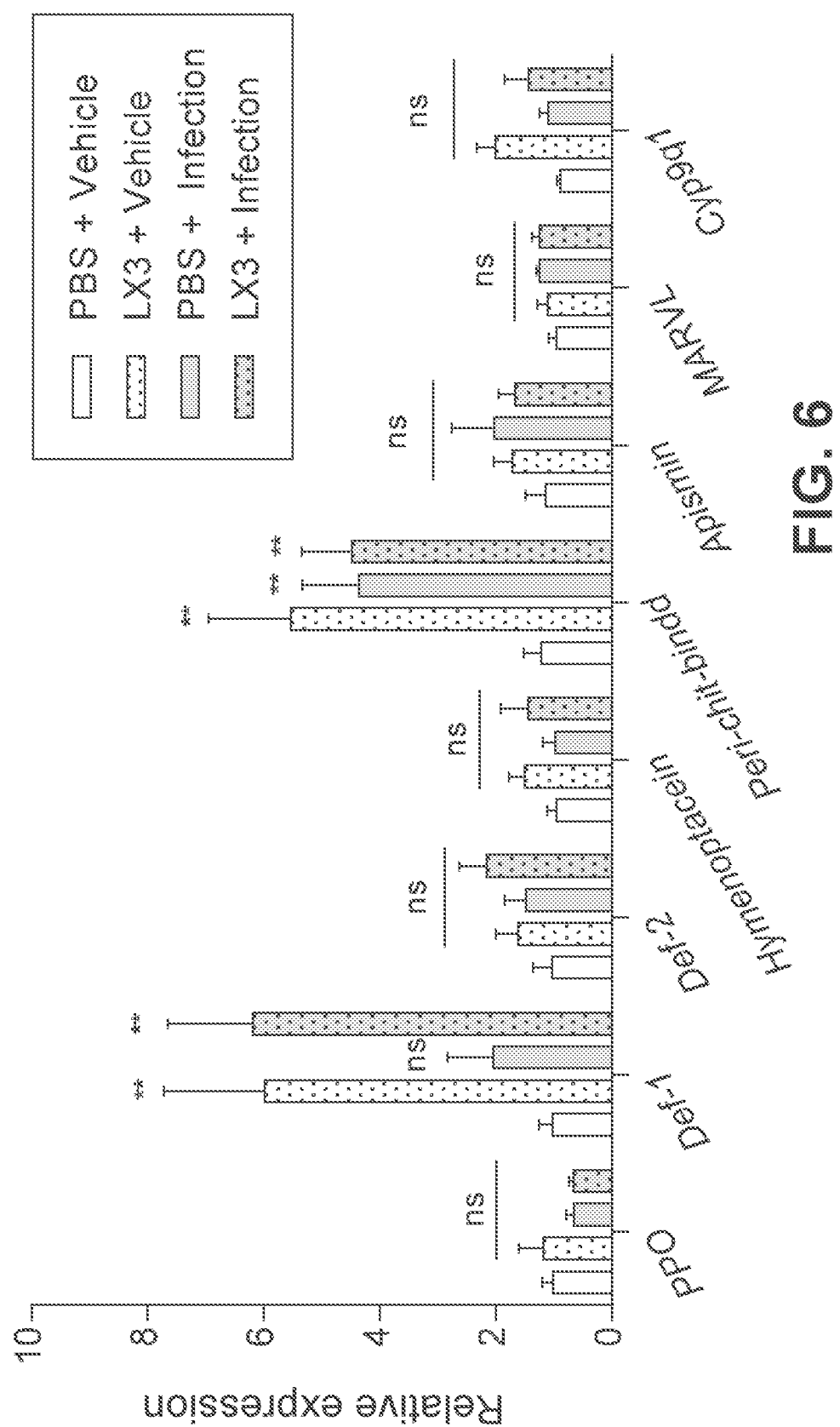
FIG. 6. shows that LX3 increases immune-related gene expression during *P. larvae* infection. First-instar honey bee larvae were orally supplemented with LX3 (*Lactobacillus plantarum* Lp39, *Lactobacillus rhamnosus* GR-1, and *Lactobacillus kunkeei* BR-1) or vehicle for 24 h, followed by inoculation with $10^4$ spores of *P. larvae*. Expression of immune-related and cellular-response genes were quantified via RT-qPCR at 72 h post-infection. All statistical comparisons are relative to the non-infected PBS control group and calculated with raw ΔΔCt values. Mean±standard deviation (one-way ANOVA with Holm-Sidak's multiple comparisons) of 6 larvae per treatment group with technical duplicate repeats are shown. ns=not significant, *p<0.05, p<0.01, and *p<0.001.
Figure 7:
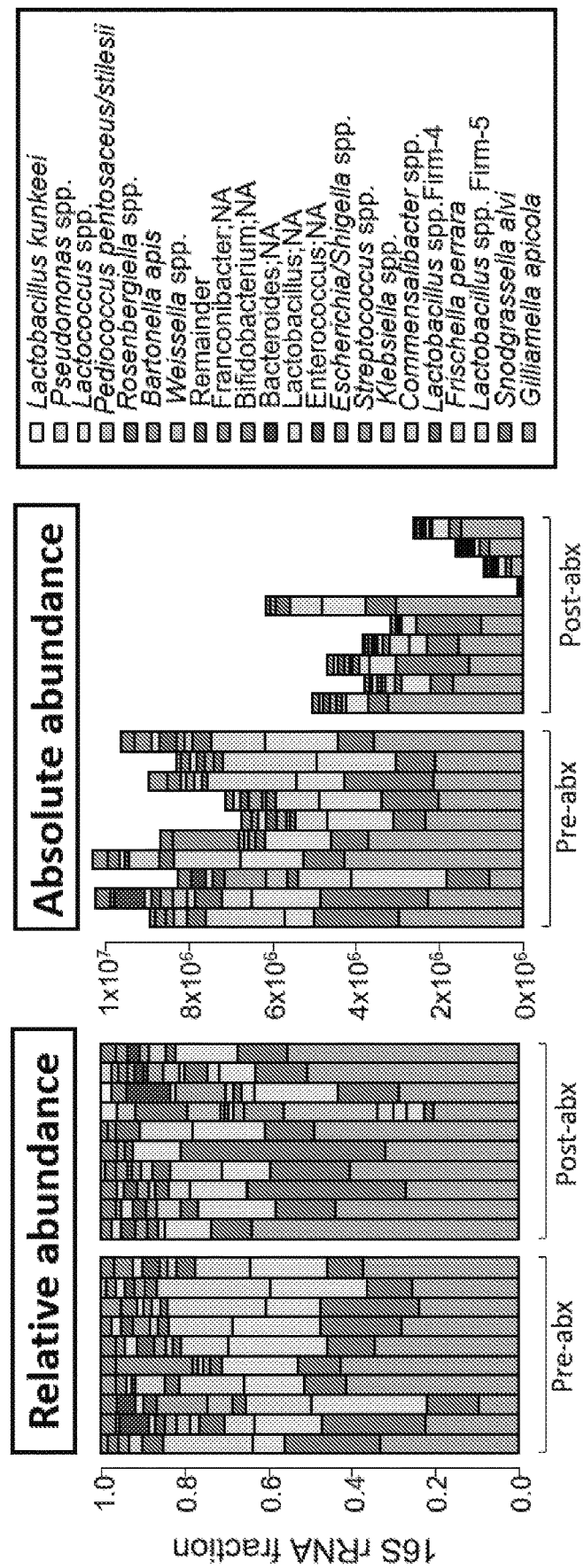
FIG. 7. shows compositional and absolute abundance differences in adult gut microbiota at week 0 (Pre-abx) and week 2 (Post-abx) of oxytetracycline treatment. Bar plots represent the gut microbiota compositions of adult nurse bees as determined by sequencing of the V4 region of the bacterial 16S rRNA gene. Taxonomy was assigned using a custom database created by combining a previously established dataset of bee-associated 16S rRNA gene sequences with the SILVA NR v132 training set.
Figure 8A:
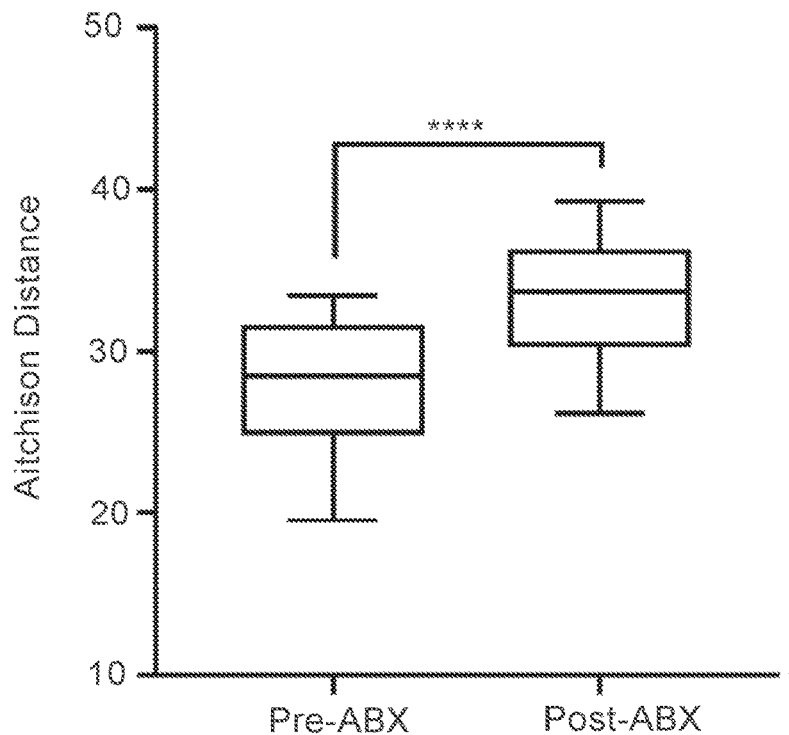
FIGS. 8A-8B show beta diversity scores of adult honey bee gut microbiota compositions. Beta diversity of adult honey bee gut microbiota composition was analyzed on week 0 (Pre-ABX) and week 2 (Post-ABX) during oxytetracycline treatment.
Figure 8B:
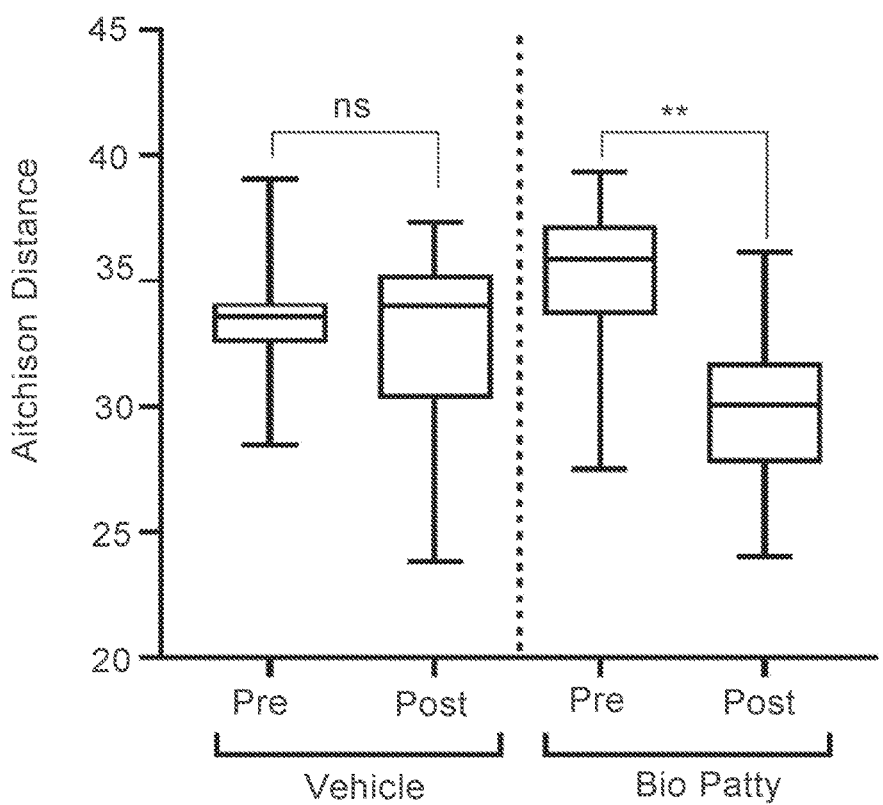
Figure 9A:
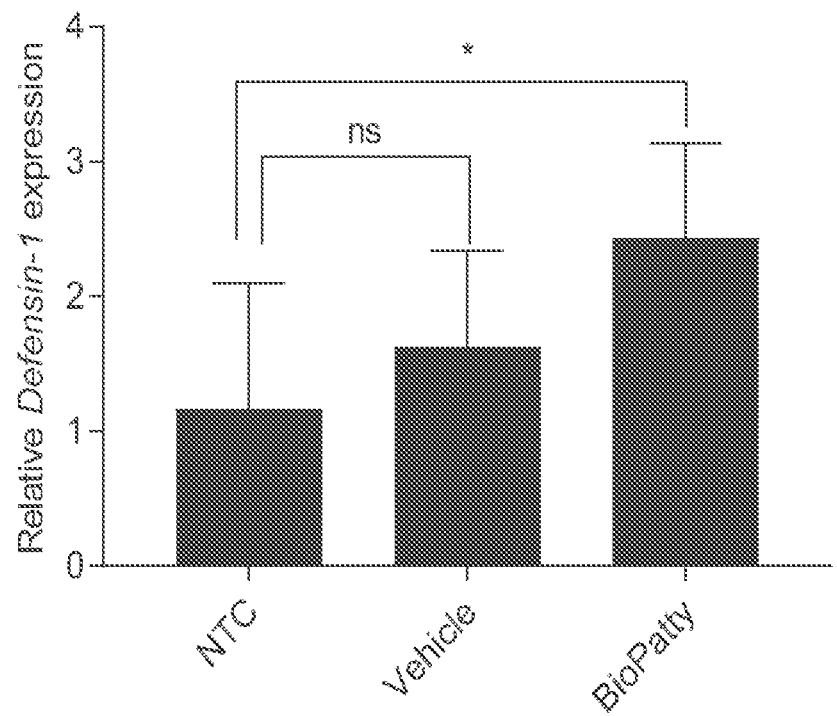
FIGS. 9A-9D show qPCR-based gene expression of adult honey bee heads following 28 days no treatment, vehicle patty supplementation, or BioPatty supplementation.
Figure 9B:
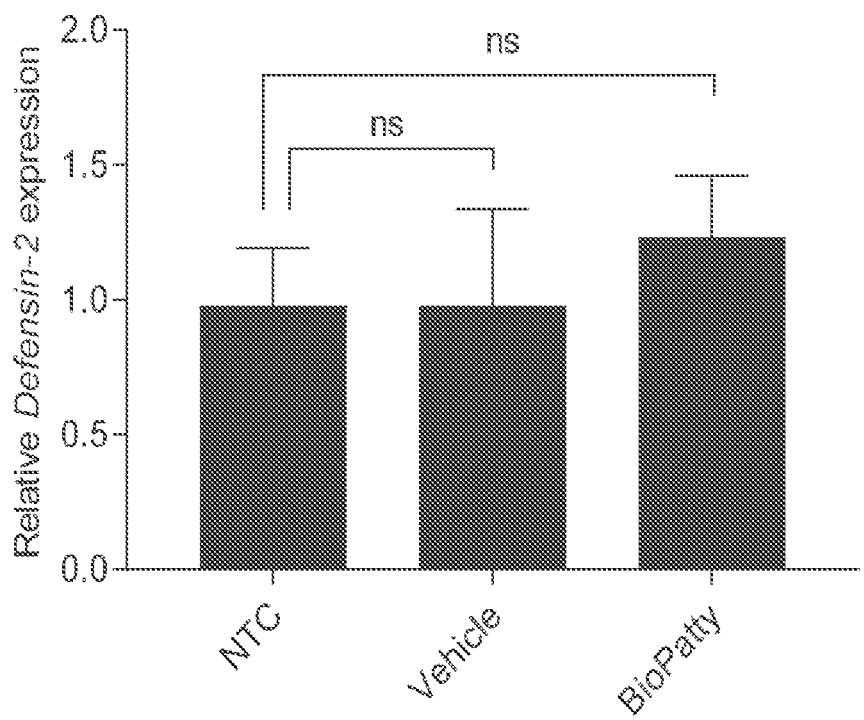
Figure 9C:
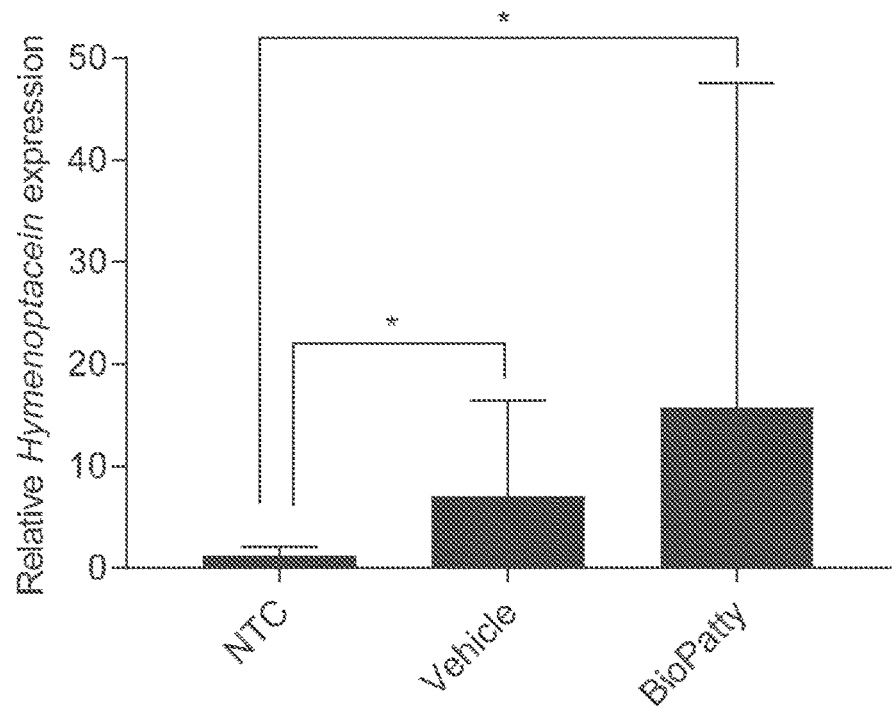
Figure 9D:
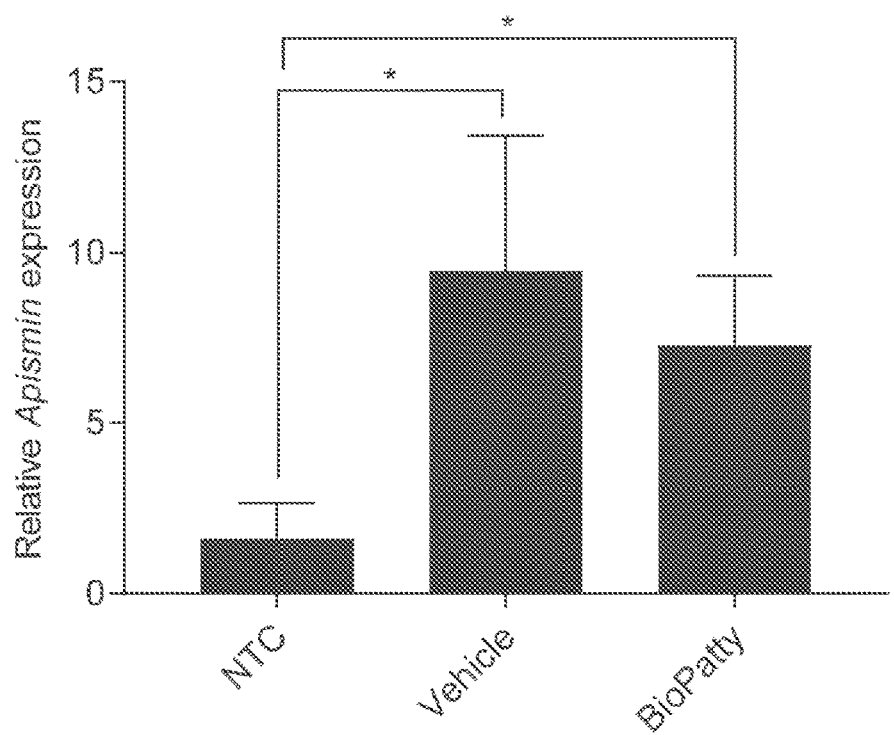
Figure 10A:
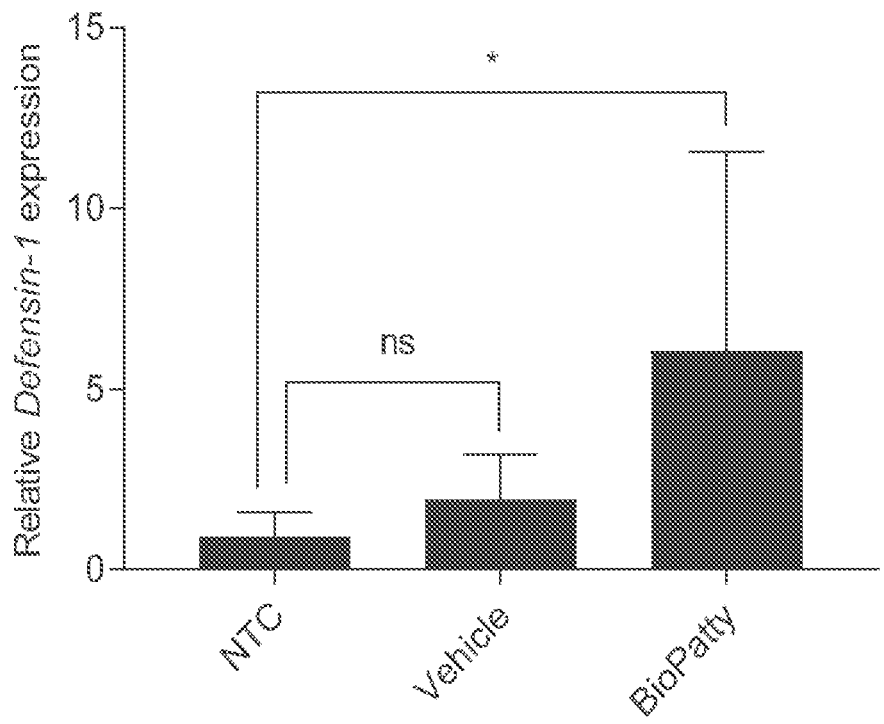
FIGS. 10A-10D. shows qPCR-based gene expression of adult honey bee guts following 28 days no treatment, vehicle patty supplementation, or BioPatty supplementation.
Figure 10B:
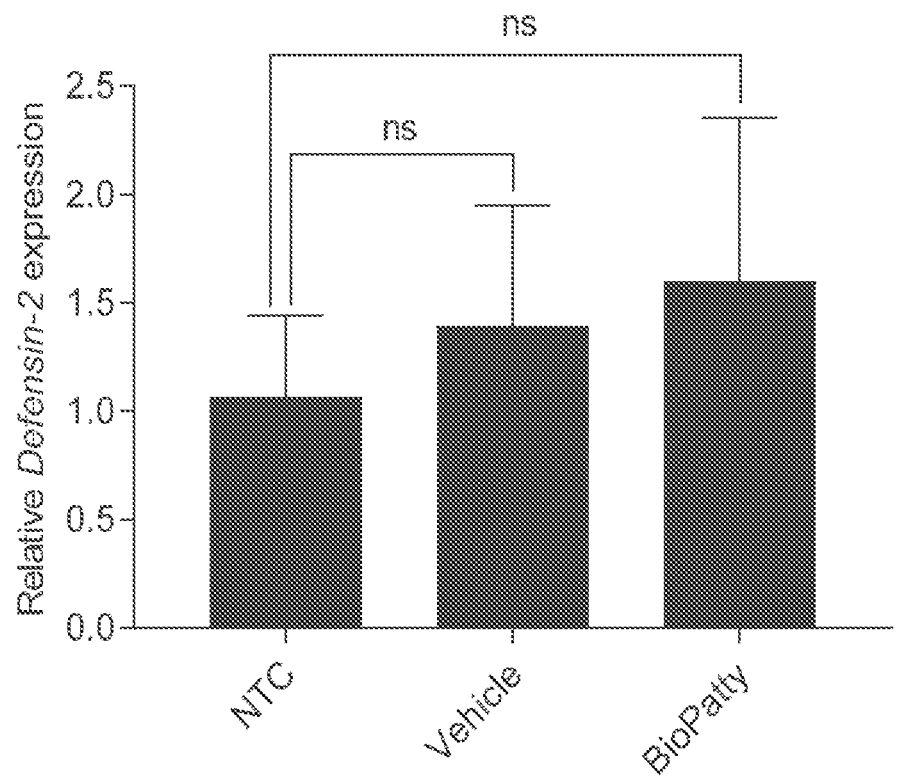
Figure 10C:
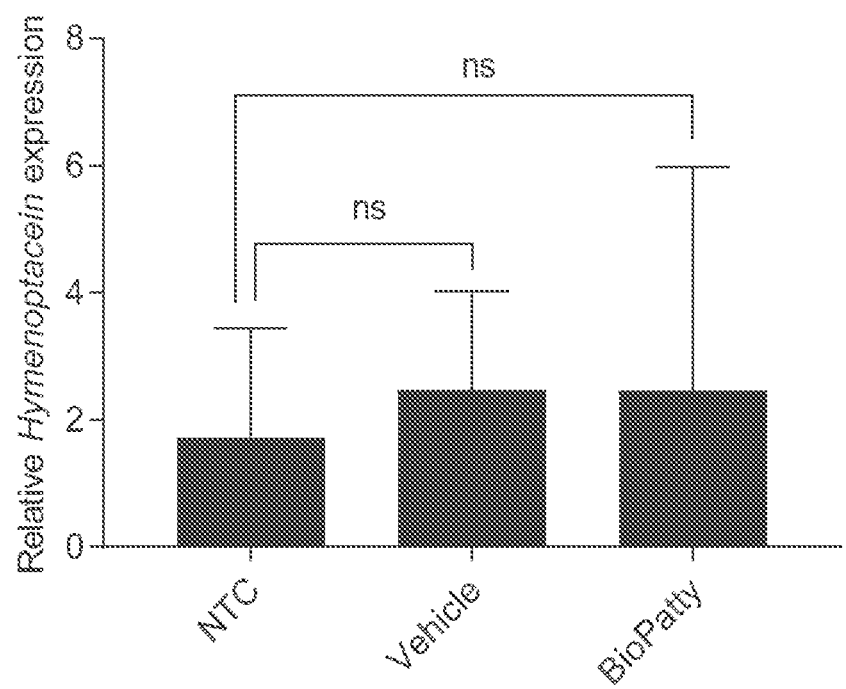
Figure 10D:
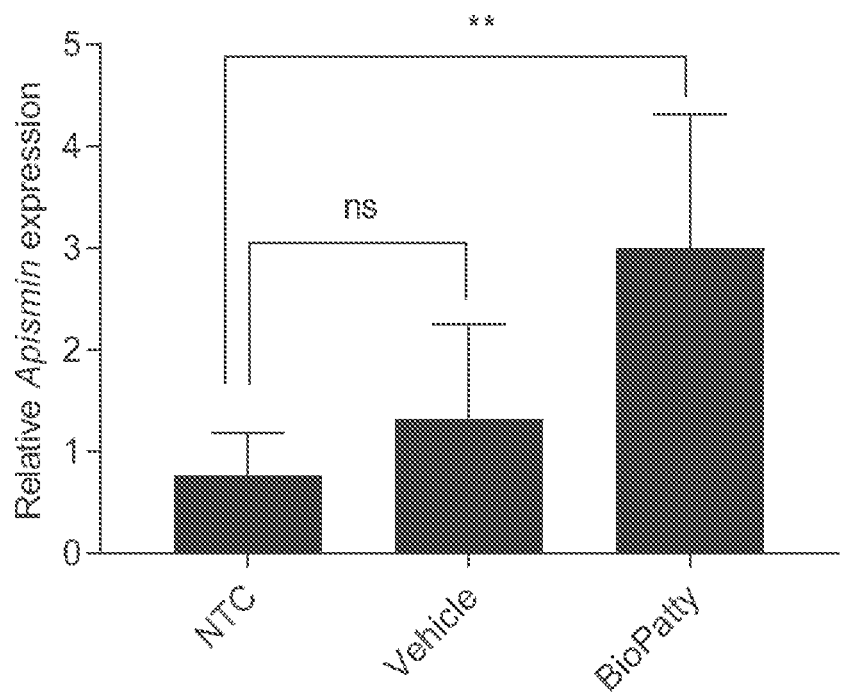

Example 20. LX3 Increases Immune-Related Gene Expression During *P. larvae* Infection Increased expression of key immune-related genes has been shown to parallel very closely with the ability of honey bee larvae to resist *P. larvae* infection. Here, prophylactic supplementation with LX3 (24 h) significantly upregulated Def-1 and Pcbd at 72 h post-infection compared to PBS-supplemented controls (one-way ANOVA with Holm-Sidak's multiple comparisons, P=0.0079 and P=0.0110, respectively; FIG. 6). LX3 administration alone also significantly increased expression of these genes in the absence of *P. larvae* inoculation (one-way ANOVA with Holm-Sidak's multiple comparisons, P=0.0146 and P=0.0106, respectively), compared to PBS-supplemented controls. No changes were observed in Ppo, Def-2, *Hymenoptacein*, or *Apismin* (FIG. 6).

Endnotes

While embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives described herein may be employed in practicing the disclosure. It is intended that the following claims define the scope and that methods and structures within the scope of these claims and their equivalents be covered thereby.

What is claimed is:

1. A method of using a composition for protecting honeybees from a pesticide, comprising administering to a hive in need thereof a composition that includes at least one *Lactobacillus* strain wherein said composition is included in a pollen patty, wherein the at least one *Lactobacillus* strain comprises *Lactobacillus rhamnosus* GR-1, and wherein the pesticide is selected from the group consisting of acetamiprid, clothianidin, dinotefuran, nitenpyram, thiacloprid, and thiamethoxam.

2. A method of using a composition for protecting honeybees from a pesticide, comprising administering to a hive in need thereof a composition that includes at least one *Lactobacillus* strain said *Lactobacillus* strain comprising *Lactobacillus rhamnosus* GR-1, wherein the composition is formulated for application as an isotonic spray, and wherein the pesticide is selected from the group consisting of acetamiprid, clothianidin, dinotefuran, nitenpyram, thiacloprid, and thiamethoxam.

3. A method of treating disease in honeybees associated with exposure to a pesticide, comprising providing a composition that includes at least one *Lactobacillus* strain to a honeybee hive in need thereof, said *Lactobacillus* strain comprising *Lactobacillus rhamnosus* GR-1, and wherein the pesticide is selected from the group consisting of acetamiprid, clothianidin, dinotefuran, nitenpyram, thiacloprid, and thiamethoxam.

4. The method as set forth in claim 3, wherein the composition further comprises a sugar source, and a protein source.

5. The method as set forth in claim 3, wherein the composition further comprises a sugar source selected from the group consisting of sugar syrup, solid sugar, or a combination thereof.

6. The method as set forth in claim 3, wherein the composition further comprises a protein source selected from the group consisting of soy flour, and brewer's yeast, or a combination thereof.

7. The method as set forth in claim 3, wherein the composition is included in a pollen patty that comprises bee pollen.

8. The method as set forth in claim 3, wherein said composition further comprises:
   a protein source selected from the group consisting of soy flour, yeast, yeast-extract, pollen, and combinations thereof,
   an amino acid selected from the group consisting of arginine, histidine, isoleucine, leucine, lysine, methionine, phenylalanine, threonine, tryptophan, and valine, and combinations thereof; and
   a carbohydrate source selected from the group consisting of sugar syrup, cane sugar, beet sugar, corn syrup, honey, malt, glucose, fructose, sucrose, trehalose, maltose, melezitose, and combinations thereof.

9. The method as set forth in claim 3, wherein the composition comprises a protein source selected from the group consisting of soy flour and brewer's yeast, or a combination thereof.

10. The method as set forth in claim 3, further comprising administering to the hive an antioxidant, oil, or preservative.

* * * * *

SEQUENCE LISTING

```
<160> NUMBER OF SEQ ID NOS: 24

<210> SEQ ID NO 1
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 1
gcacgtgaag atctagcagc tc                                           22

<210> SEQ ID NO 2
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 2
aattatttgg tcgctggaat tg                                           22

<210> SEQ ID NO 3
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 3
ttgctctgta aggttgtttt gc                                           22

<210> SEQ ID NO 4
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 4
cacggataca tcctgcagtc atc                                          23

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
tgcgctgcta actgtctcag                                              20

<210> SEQ ID NO 6
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
gcaactaccg cctttacgtc                                                    20

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
agatggcatg catttgttga                                                    20

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
ctcttctgtg ccgttgcata                                                    20

<210> SEQ ID NO 9
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 9
gcaaacgaga tttcaatggc aatcttcag                                          29

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
tgagcaaaat cgttgctgtc                                                    20

<210> SEQ ID NO 11
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 11
gaaatgttga atacatcgat attcaccgta c                                       31

<210> SEQ ID NO 12
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 12
```

```
atcctggcca agtgcagctt c                                              21

<210> SEQ ID NO 13
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 13
gcaccttctc cttcaccttc ag                                             22

<210> SEQ ID NO 14
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 14
taacgtccag cagaatgtgg ta                                             22

<210> SEQ ID NO 15
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 15
tgtctggtta actacaaatc cttctg                                         26

<210> SEQ ID NO 16
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 16
gagaatgacg agatacagaa ctgtcac                                        27

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
aatggcactt aaccgaaacg                                                20

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 18
gggtaacgtg cgacgtttta                                                20

<210> SEQ ID NO 19
<211> LENGTH: 20
<212> TYPE: DNA
```

```
<213> ORGANISM: Artificial Sequence
<220> FEATURE:
<223> OTHER INFORMATION: synthetic oligonucleotide

<400> SEQUENCE: 19
ccacgctcgt cttctttagg                                              20

<210> SEQ ID NO 20
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 20
cgtctcctgt cattccatt                                               19

<210> SEQ ID NO 21
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 21
cacattggta attgtatagt acgttcgcat c                                 31

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
aacgacatcc acgttcgatt                                              20

<210> SEQ ID NO 23
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 23
ctccattcca cgtagaggaa gtatgtc                                      27

<210> SEQ ID NO 24
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 24
cagctccttc aattggatca gcaac                                        25
```